US010603000B2

(12) United States Patent
Hattori et al.

(10) Patent No.: US 10,603,000 B2
(45) Date of Patent: Mar. 31, 2020

(54) RADIOGRAPHY SYSTEM AND METHOD FOR OPERATING RADIOGRAPHY SYSTEM

(71) Applicant: FUJIFILM Corporation, Tokyo (JP)

(72) Inventors: Masato Hattori, Ashigarakami-gun (JP); Ryo Imamura, Ashigarakami-gun (JP); Haruyasu Nakatsugawa, Ashigarakami-gun (JP); Koichi Kitano, Ashigarakami-gun (JP); Naoyuki Nishino, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 14 days.

(21) Appl. No.: 16/059,673

(22) Filed: Aug. 9, 2018

(65) Prior Publication Data
US 2019/0046140 A1    Feb. 14, 2019

(30) Foreign Application Priority Data
Aug. 10, 2017   (JP) .................................. 2017-156065

(51) Int. Cl.
*A61B 6/00*    (2006.01)
*A61B 6/08*    (2006.01)

(52) U.S. Cl.
CPC ................ *A61B 6/469* (2013.01); *A61B 6/08* (2013.01); *A61B 6/4283* (2013.01); *A61B 6/4405* (2013.01); *A61B 6/4494* (2013.01); *A61B 6/461* (2013.01); *A61B 6/465* (2013.01); *A61B 6/468* (2013.01); *A61B 6/48* (2013.01); *A61B 6/5294* (2013.01); *A61B 6/54* (2013.01); *A61B 6/545* (2013.01); *A61B 6/547* (2013.01); *A61B 6/587* (2013.01); *A61B 6/588* (2013.01); *A61B 6/542* (2013.01); *A61B 6/563* (2013.01)

(58) Field of Classification Search
CPC ..... A61B 6/4405; A61B 6/4494; A61B 6/461; A61B 6/465; A61B 6/468; A61B 6/48; A61B 6/5294; A61B 6/54; A61B 6/545; A61B 6/547; A61B 6/587; A61B 6/588; A61B 6/542; A61B 6/563
USPC ............................................................ 378/62
See application file for complete search history.

(56) References Cited

U.S. PATENT DOCUMENTS

| 5,539,798 A | * | 7/1996 | Asahina | A61B 6/022 |
| | | | | 348/E5.086 |
| 2002/0012450 A1 | * | 1/2002 | Tsujii | H04N 5/32 |
| | | | | 382/103 |
| 2009/0214220 A1 | * | 8/2009 | Nishino | H04B 10/1143 |
| | | | | 398/130 |

(Continued)

FOREIGN PATENT DOCUMENTS

| JP | 6-217973 A | 8/1994 |
| JP | 2012-24399 A | 2/2012 |

*Primary Examiner* — Taeho Jo
(74) *Attorney, Agent, or Firm* — Birch, Stewart, Kolasch & Birch, LLP

(57) ABSTRACT

In the radiography system, a camera provided in an X-ray source captures a camera image indicating a usage environment in which an electronic cassette is used. The electronic cassette is inserted into the field of view of the camera. An in-image cassette region of the electronic cassette is detected from the camera image. A cassette ID of the electronic cassette is acquired from the in-image cassette region. The acquired cassette ID is collated with registration information set in a console and a use cassette setting process is performed on the basis of the collation result.

18 Claims, 31 Drawing Sheets

(56) References Cited

U.S. PATENT DOCUMENTS

| | | | |
|---|---|---|---|
| 2010/0054416 A1* | 3/2010 | Tsubota | A61B 6/00 378/98 |
| 2010/0061616 A1* | 3/2010 | Tsubota | A61B 6/00 382/132 |
| 2010/0079273 A1* | 4/2010 | Tsubota | H04W 48/02 340/539.1 |
| 2010/0243910 A1* | 9/2010 | Tsubota | A61B 6/4283 250/393 |
| 2011/0110494 A1* | 5/2011 | Lee | G03B 42/04 378/98 |
| 2012/0250825 A1* | 10/2012 | Yoshida | A61B 6/4233 378/91 |
| 2013/0114793 A1 | 5/2013 | Ohta et al. | |
| 2013/0121468 A1* | 5/2013 | Ohta | A61B 6/4405 378/63 |
| 2013/0259196 A1* | 10/2013 | Tajima | A61B 6/42 378/62 |
| 2013/0322599 A1* | 12/2013 | Watanabe | A61B 6/4283 378/91 |
| 2014/0275954 A1* | 9/2014 | Ohta | G16H 40/63 600/407 |
| 2014/0276056 A1* | 9/2014 | Ohta | A61B 6/465 600/440 |
| 2015/0078527 A1* | 3/2015 | Iwamoto | A61B 6/563 378/91 |
| 2015/0222134 A1* | 8/2015 | Ikegame | H02J 7/0045 320/107 |
| 2015/0279196 A1* | 10/2015 | Tajima | G08B 13/22 340/539.32 |
| 2016/0015340 A1* | 1/2016 | Nenoki | A61B 6/4283 378/98 |
| 2016/0081650 A1* | 3/2016 | Okusu | A61B 6/56 378/62 |
| 2016/0174918 A1* | 6/2016 | Wang | A61B 6/4405 378/63 |
| 2017/0135667 A1* | 5/2017 | Becker | A61B 6/4411 |
| 2017/0219498 A1* | 8/2017 | Chtcheprov | G01N 23/046 |

* cited by examiner

| REGISTERED CASSETTE INFORMATION | | | | |
|---|---|---|---|---|
| CASSETTE ID | NAME | SIZE | COMMUNICATION ADDRESS | SPECIFICATION INFORMATION |
| DR0001 | CASSETTE A | 14 × 17 TYPE | adr0001 | 📄 |
| DR0002 | CASSETTE B | 10 × 12 TYPE | adr0002 | 📄 |
| DR0003 | CASSETTE C | 14 × 17 TYPE | adr0003 | 📄 |
| DR0004 | CASSETTE D | 17 × 17 TYPE | adr0004 | 📄 |
| DR0005 | CASSETTE E | 14 × 17 TYPE | adr0005 | 📄 |

| USE CASSETTE SETTING INFORMATION | | | | |
|---|---|---|---|---|
| CASSETTE ID | NAME | SETTING INFORMATION | STATUS | IMAGING ORDER |
| DR0001 | CASSETTE A | UNSET | - | - |
| DR0002 | CASSETTE B | UNSET | - | - |
| DR0003 | CASSETTE C | UNSET | - | - |
| DR0004 | CASSETTE D | UNSET | - | - |
| DR0005 | CASSETTE E | UNSET | - | - |

FIG. 8

| ORDER ID | SUBJECT ID | IMAGING MENU | COMPLETION INFORMATION | USE CASSETTE |
|---|---|---|---|---|
| OD0001 | P0400 | CHEST/UPRIGHT POSITION/FRONT | IMAGING COMPLETED | DR0001 |
| OD0002 | P0500 | ABDOMEN/DECUBITUS POSITION/FRONT | UNCOMPLETED | - |
| OD0003 | P0600 | CHEST/UPRIGHT POSITION/FRONT | UNCOMPLETED | - |

| REGISTERED CASSETTE INFORMATION | | | | |
|---|---|---|---|---|
| CASSETTE ID | NAME | SIZE | COMMUNICATION ADDRESS | SPECIFICATION INFORMATION |
| DR0001 | CASSETTE A | 14 × 17 TYPE | adr0001 | |
| DR0002 | CASSETTE B | 10 × 12 TYPE | adr0002 | |
| DR0003 | CASSETTE C | 14 × 17 TYPE | adr0003 | |
| DR0004 | CASSETTE D | 17 × 17 TYPE | adr0004 | |
| DR0005 | CASSETTE E | 14 × 17 TYPE | adr0005 | |

USE CASSETTE SELECTION SCREEN (69), 57

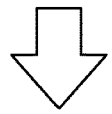

(B)

63
- IMAGING ORDER "OD0001"
  IMAGING MENU: CHEST, UPRIGHT POSITION, FRONT
  CASSETTE ID "DR0001"  NAME "A"  — 63a
- IMAGING ORDER "OD0002"
  IMAGING MENU: ABDOMEN, DECUBITUS POSITION, FRONT
  CASSETTE ID "DR0003"  NAME "C"  — 63a
- IMAGING ORDER "OD0003"
  IMAGING MENU: ABDOMEN, DECUBITUS POSITION, FRONT  — 63a

| REGISTERED CASSETTE INFORMATION ||||| 
|---|---|---|---|---|
| CASSETTE ID | NAME | SIZE | COMMUNICATION ADDRESS | SPECIFICATION INFORMATION |
| DR0003 | CASSETTE C | 14 × 17 TYPE | adr0003 | |

58

| USE CASSETTE SETTING INFORMATION |||||
|---|---|---|---|---|
| CASSETTE ID | NAME | SETTING INFORMATION | STATUS | IMAGING ORDER |
| DR0001 | CASSETTE A | UNSET | – | – |
| DR0002 | CASSETTE B | UNSET | – | – |
| DR0003 | CASSETTE C | SET | READY | OD0002 |
| DR0004 | CASSETTE D | UNSET | – | – |
| DR0005 | CASSETTE E | UNSET | – | – |

59

| ORDER ID | SUBJECT ID | IMAGING MENU | COMPLETION INFORMATION | USE CASSETTE |
|---|---|---|---|---|
| OD0001 | P0400 | CHEST/SEATED POSITION/FRONT | IMAGING COMPLETED | DR0001 |
| OD0002 | P0500 | ABDOMEN/DECUBITUS POSITION/FRONT | UNCOMPLETED | – |

FIG. 15
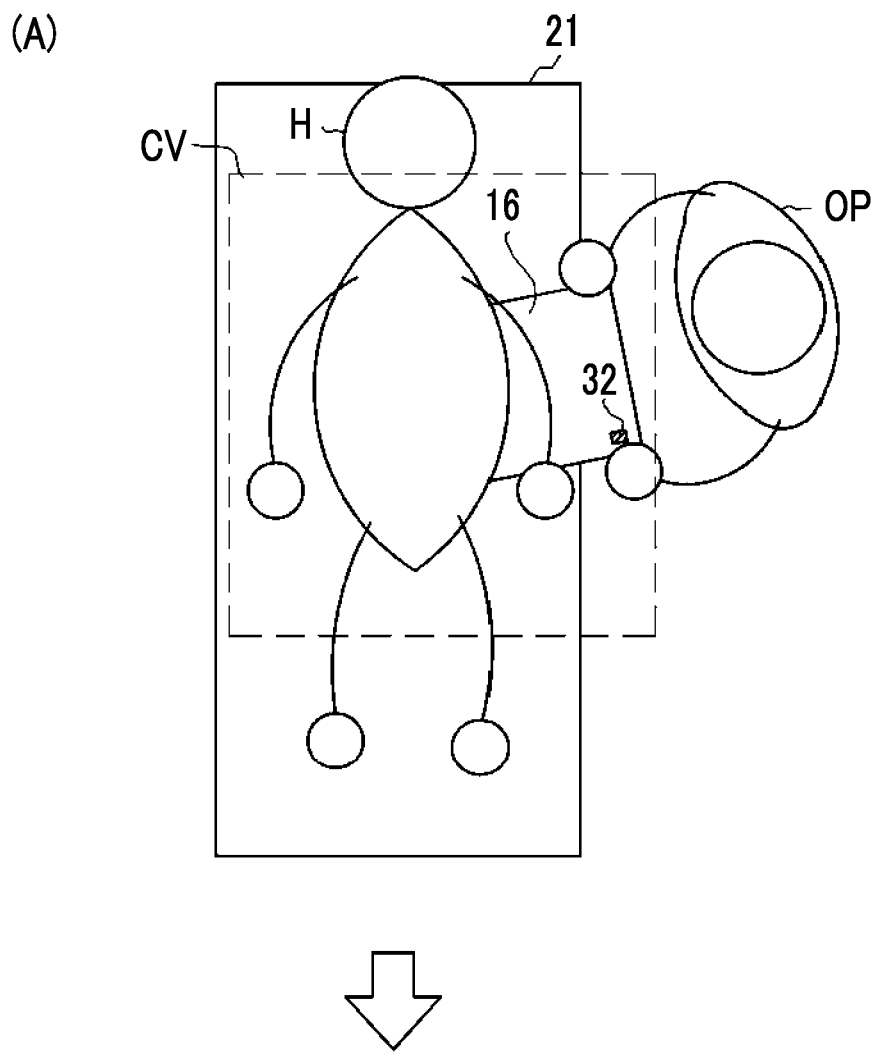
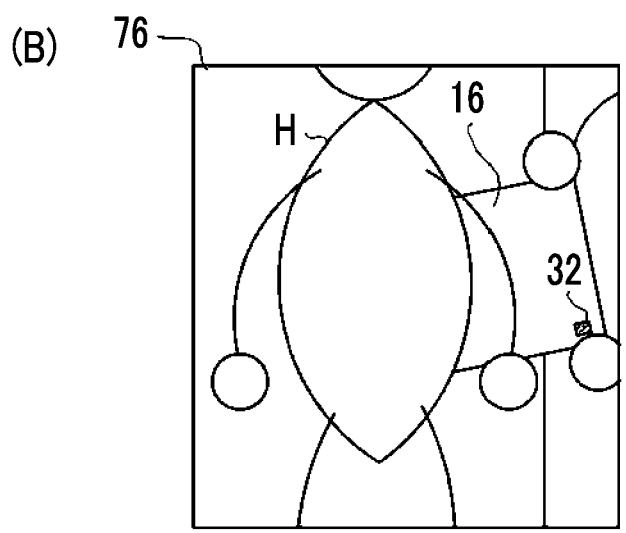

| USE CASSETTE SETTING INFORMATION ||||| 
|---|---|---|---|---|
| CASSETTE ID | NAME | SETTING INFORMATION | STATUS | IMAGING ORDER |
| DR0001 | CASSETTE A | UNSET | - | - |
| DR0002 | CASSETTE B | UNSET | - | - |
| DR0003 | CASSETTE C | SET | READY | OD0002 |
| DR0004 | CASSETTE D | UNSET | - | - |
| DR0005 | CASSETTE E | UNSET | - | - |

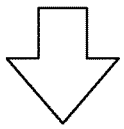

58

| USE CASSETTE SETTING INFORMATION |||||
|---|---|---|---|---|
| CASSETTE ID | NAME | SETTING INFORMATION | STATUS | IMAGING ORDER |
| DR0001 | CASSETTE A | UNSET | READY | OD0002 |
| DR0002 | CASSETTE B | UNSET | - | - |
| DR0003 | CASSETTE C | SET | - | - |
| DR0004 | CASSETTE D | UNSET | - | - |
| DR0005 | CASSETTE E | UNSET | - | - |

FIG. 34
(A)
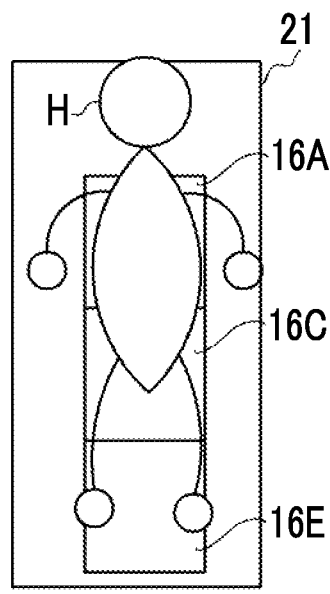
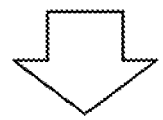
(B)
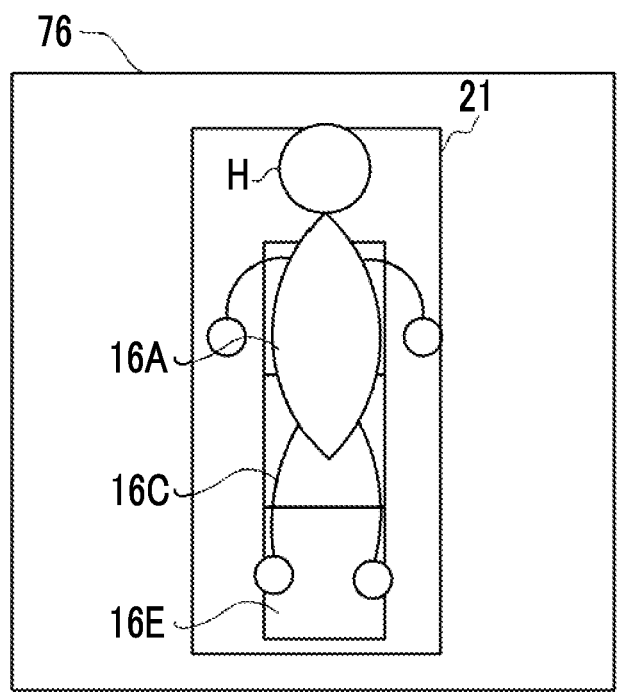

RADIOGRAPHY SYSTEM AND METHOD FOR OPERATING RADIOGRAPHY SYSTEM

CROSS-REFERENCE TO RELATED APPLICATION

This application claims priority under 35 USC 119 from Japanese Patent Application No. 2017-156065, filed 10 Aug. 2017, the disclosure of which is incorporated by reference herein.

BACKGROUND OF THE INVENTION

1. Field of the Invention

The present invention relates to a radiography system that performs radiography using an electronic cassette and a method for operating the radiography system.

2. Description of the Related Art

In a medical field, a diagnosis is made on the basis of a radiographic image detected by a radiographic image detection device. The radiographic image detection device includes a sensor panel. The sensor panel is provided with an imaging region. A plurality of pixels are two-dimensionally arranged in the imaging region. The pixel is sensitive to radiation which has been emitted from a radiation generation apparatus and then transmitted through a subject (patient) and accumulates charge. The radiographic image detection device converts the charge accumulated in the pixel into a digital signal and outputs the digital signal as a radiographic image.

The radiographic image detection devices are classified into a fixed type that is fixed to an imaging stand installed in an imaging room and a portable type in which, for example, a sensor panel is accommodated in a portable housing. The portable radiographic image detection device is referred to as an electronic cassette. The electronic cassettes are classified into a wired type that is supplied with power from a commercial power supply through a cable and a wireless type that is supplied with power from a battery provided in a housing.

The electronic cassette is used in various environments. The electronic cassette is used in the imaging room. In many cases, the electronic cassette is carried out of the imaging room and is then used since it has high mobility. For example, the electronic cassette is used for visit imaging in which an operator visits a hospital room in which a patient who is not able to move to the imaging room is present and takes a radiographic image. In addition, the electronic cassette is used in places other than medical facilities in order to capture a radiographic image of an aged person who gets medical treatment at home or a patient who is in an emergency condition due to an accident or a disaster. Hereinafter, imaging without using an imaging stand is referred to as free imaging.

In a preparation operation before radiography, an operator, such as a radiology technician, relatively positions a radiation generation apparatus, an electronic cassette, and a patient. After positioning is completed, the operator operates the radiation generation apparatus to emit radiation and takes a radiographic image. JP2012-024399A (corresponding to US2013/114793A1) and JP1994-217973 (JP-H06-217973A, corresponding to U.S. Pat. No. 5,539,798A) disclose a technique which appropriately assists positioning using an optical camera that captures an image of a patient or an electronic cassette in the direction in which the radiation generation apparatus is disposed. For example, guide lines for positioning are inserted into a camera image captured by the camera and the camera image is displayed on a display unit. The operator can perform positioning while seeing the guide lines.

SUMMARY OF THE INVENTION

However, in a case in which the electronic cassettes are used, a plurality of electronic cassettes may be present in the usage environment. For example, in many cases, a plurality of electronic cassettes with different sizes or purposes are provided in the imaging room. During visit imaging, in some cases, a treatment cart is provided with a plurality of electronic cassettes and a plurality of electronic cassettes are carried in a hospital room which is the usage environment.

In a case in which the electronic cassette is the wireless type, an operation of pairing the electronic cassette used for imaging and a console needs to be performed before imaging. The console is a control device that controls the electronic cassette or acquires a radiographic image from the electronic cassette. The pairing means an operation of setting, as a use cassette, an electronic cassette used for imaging, that is, an electronic cassette selected as a communication partner of the console during imaging in the console.

For example, information of a plurality of electronic cassettes which are the candidates of the electronic cassette used for imaging is registered in the console in advance. During imaging, the operator operates an operation screen of the console to select an electronic cassette to be used for imaging from the plurality of registered electronic cassettes (hereinafter, referred to as registered cassettes). The console receives the selection operation of the operator and sets the electronic cassette selected by the operator as the use cassette. In this way, pairing is performed. The pairing is performed through the operation screen of the console.

In the actual imaging spot, the paired use cassette is frequently changed to another electronic cassette. For example, during positioning, the operator sees the body type of a patient, feels that the size of the paired use cassette is small, and changes the use cassette to another electronic cassette with a large size. In a case in which the remaining battery level of the use cassette is low immediately before imaging, the operator changes the use cassette to another electronic cassette with a high remaining battery level. In this case, it is necessary to perform a direct consol operation of moving to the place in which the console is present and operating the operation screen. Therefore, it takes a lot of time and effort for pairing.

In a case in which visit imaging is performed, for example, the console is provided in a treatment cart. During positioning, the operator stands next to the patient. In this case, the operator directly operates the console in order to change the use cassette. That is, the operator interrupts positioning, returns to the place in which the console is provided, and performs pairing again. In the case of the imaging room, the console may be provided in a preparation room different from the imaging room. In this case, it takes a lot of time and effort to move to the place in which the console is provided, which is a large burden on the operator.

JP2012-024399A and JP1994-217973 (JP-H06-217973A) disclose the technique which assists positioning, but do not disclose any solutions to the above-mentioned problems.

An object of the invention is to provide a radiography system that can simply pair an electronic cassette, without directly operating a console, and a method for operating the radiography system.

According to an aspect of the invention, there is provided a radiography system comprising an electronic cassette, a console, a camera image acquisition unit, an in-image cassette detection unit, an identification information acquisition unit, a collation unit, and a use cassette setting unit. The electronic cassette detects a radiographic image based on radiation which has been emitted from a radiation generation apparatus and transmitted through a subject. The console communicates with a use cassette that is selected from registered cassettes, which are the electronic cassettes registered in advance, and is set as the electronic cassette used for radiography to acquire the radiographic image from the use cassette. The camera image acquisition unit acquires a camera image, which is obtained by capturing a usage environment including a place in which the electronic cassette is used and a periphery of the place, from an optical camera that captures the usage environment. The in-image cassette detection unit detects the electronic cassette included in the camera image on the basis of the camera image. The identification information acquisition unit acquires identification information of the electronic cassette detected from the camera image. The collation unit collates the identification information with registration information of the registered cassettes registered in the console. The use cassette setting unit determines whether the electronic cassette included in the camera image is the registered cassette on the basis of a collation result of the collation unit and sets the electronic cassette determined to be the registered cassette as the use cassette.

The camera image is, for example, a motion picture or a still image.

For example, the camera is provided in the radiation generation apparatus or is provided in a room in a case in which the usage environment is an indoor environment.

Preferably, the identification information includes a cassette ID which includes a character string uniquely given to each electronic cassette.

Preferably, in a case in which an ID marker indicating the cassette ID is attached to an outer surface of the electronic cassette, the identification information acquisition unit detects the ID marker from the camera image and acquires the cassette ID and the collation unit collates the cassette ID with the registration information.

In a case in which a light source that emits identification light which is light indicating the identification information is provided in the electronic cassette, the identification information acquisition unit may detect the identification light from the camera image and acquire the identification information.

Preferably, the identification light is identified on the basis of at least one of a color, a lighting pattern, or a lighting time.

The radiography system may further comprise: a direction detection unit that detects a direction in which the electronic cassette is present in the usage environment on the basis of the camera image; and a request signal transmission unit that transmits an identification information request signal for requesting the identification information to the electronic cassette. In a case in which the electronic cassette is included in the camera image, the request signal transmission unit may transmit the identification information request signal in the direction detected by the direction detection unit and receive the identification information as a response from the electronic cassette. The identification information acquisition unit may acquire the identification information received by the request signal transmission unit.

In a case in which the response is not received, the identification information acquisition unit may transmit, to the electronic cassette, a status change command to change a status of the electronic cassette to a status in which the electronic cassette is capable of responding to the identification information request signal.

The identification information acquisition unit may output a warning in a case in which the electronic cassette is included in the camera image, but the identification information is not capable of being acquired from the electronic cassette.

Preferably, in a case in which the electronic cassette detected in the camera image has been set as the use cassette, the use cassette setting unit notifies that the electronic cassette detected in the camera image has been set as the use cassette through a notification unit.

Preferably, the notification unit is provided in the radiation generation apparatus.

In a case in which the electronic cassette is included in the camera image, but is not the registered cassette, the use cassette setting unit may output a warning indicating that the electronic cassette is not the registered cassette.

In a case in which the electronic cassette is included in the camera image, but is not the registered cassette, the use cassette setting unit may perform a process of inquiring whether to register the electronic cassette as the registered cassette in the console.

In a case in which the use cassette has been set in the console and the registered cassette different from the set use cassette is newly detected from the camera image, the use cassette setting unit may change the newly detected registered cassette to the use cassette.

In a case in which the use cassette has been set in the console and the registered cassette different from the use cassette is newly detected from the camera image, the use cassette setting unit may perform a process of inquiring whether to change the newly detected registered cassette to the use cassette.

The radiography system may further comprise an imaging order acquisition unit that acquires an imaging order to perform radiography. In a case in which the electronic cassette detected in the camera image is determined to be the registered cassette, the use cassette setting unit may collate content of the imaging order with specification information of the registered cassettes registered in advance, determine suitability of the registered cassettes for the imaging order, and set the registered cassette that is suitable for the imaging order as the use cassette.

During the setting of the electronic cassette detected in the camera image as the use cassette, in a case in which the detected electronic cassette is set as the use cassette and a status of the set use cassette is in a power saving mode, the use cassette setting unit may change the status to a ready status in which radiography is capable of being performed.

According to another aspect of the invention, there is provided a method for operating a radiography system comprising an electronic cassette that detects a radiographic image based on radiation which has been emitted from a radiation generation apparatus and transmitted through a subject and a console that communicates with a use cassette that is selected from registered cassettes, which are the electronic cassettes registered in advance, and is set as the electronic cassette used for radiography to acquire the radiographic image from the use cassette. The method comprises a camera image acquisition step, an in-image cassette detection step, an identification information acquisition step, a collation step, and a use cassette setting step. In the camera image acquisition step, a camera image obtained by capturing a usage environment including a place in which the electronic cassette is used and a periphery of the place is acquired from an optical camera that captures the usage environment. In the in-image cassette detection step, the electronic cassette included in the camera image is detected on the basis of the camera image. In the identification information acquisition step, identification information of the electronic cassette detected from the camera image is acquired. In the collation step, the identification information is collated with registration information of the registered cassettes registered in the console. In the use cassette setting step, it is determined whether the electronic cassette included in the camera image is the registered cassette on the basis of a collation result in the collation step and the electronic cassette determined to be the registered cassette is set as the use cassette.

According to the invention, in a case in which the electronic cassette included in the camera image obtained by capturing the usage environment using the camera is the registered cassette, the electronic cassette included in the camera image is automatically set as the use cassette. Therefore, it is possible to set the electronic cassette as the use cassette only by inserting the electronic cassette to be used for imaging into the field of view of the camera. As a result, it is possible to simply pair the electronic cassette, without directly operating the console.

BRIEF DESCRIPTION OF THE DRAWINGS

FIG. 6 is a diagram illustrating registered cassette information.

FIG. 7 is a diagram illustrating use cassette setting information.

FIG. 8 is a diagram illustrating imaging order information.

FIG. 11 is a diagram illustrating a use cassette selection screen: (A) of FIG. 11 is a diagram illustrating the entire use cassette selection screen; and (B) of FIG. 11 is a diagram illustrating a selected imaging order display region.

FIG. 12 is a diagram illustrating the relation between various kinds of information after the use cassette is selected.

FIG. 15 is a diagram illustrating a camera image: (A) of FIG. 15 is a diagram illustrating the field of view of a camera; and (B) of 15 is a diagram illustrating a camera image corresponding to the field of view.

FIG. 25 is a diagram illustrating a method for changing a use cassette according to the second embodiment.

FIG. 34 is a diagram illustrating long-length imaging according to a sixth embodiment: (A) of FIG. 34 illustrates the actual usage of the electronic cassettes; and (B) of FIG. 34 illustrates a camera image.

DESCRIPTION OF THE PREFERRED EMBODIMENTS

First Embodiment

Figure 1:
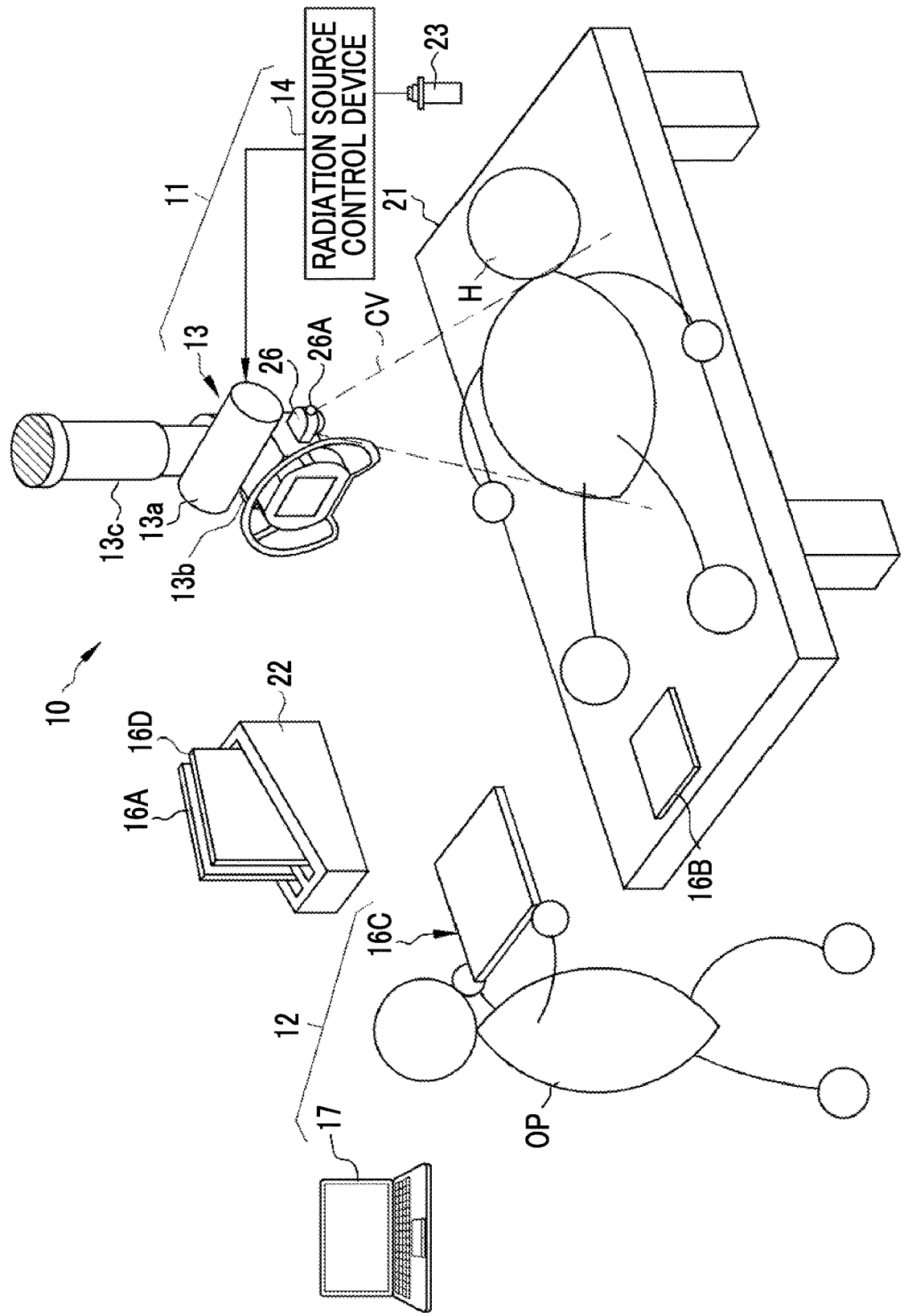
FIG. 1 is a diagram schematically illustrating the configuration of an X-ray imaging system.

In FIG. 1, an X-ray imaging system 10 that uses X-rays as radiation includes an X-ray generation apparatus 11, an X-ray imaging apparatus 12, and a camera 26. The X-ray generation apparatus 11 includes an X-ray source 13 corresponding to a radiation source and a radiation source control device 14 that controls the X-ray source 13. The X-ray imaging apparatus 12 includes an electronic cassette 16 and a console 17.

FIG. 1 illustrates an aspect in which X-ray imaging is performed for a subject H that lies on a bed 21 using the electronic cassette 16 in an imaging room in which the X-ray imaging system 10 is installed. The electronic cassette 16 is placed on, for example, the bed 21 or is held in the arms of the subject H depending on an imaging part and then imaging is performed. The X-ray imaging illustrated in FIG. 1 is free imaging without using an imaging stand.

The imaging room is equipped with an upright imaging stand (not illustrated) or a decubitus imaging stand (not illustrated) on which the electronic cassette 16 is placed in addition to the bed 21. In addition, for the electronic cassette 16, a plurality of electronic cassettes 16 having different sizes or purposes are provided. FIG. 1 illustrates, for example, an electronic cassette 16A carried by an operator OP, such as a radiology technician, that performs an imaging operation, an electronic cassette 16B that is placed on the bed 21, and electronic cassettes 16C and 16D that are accommodated in a cradle 22 with a charging function.

Hereinafter, in a case in which the electronic cassettes 16A to 16D need to be distinguished from each other, the electronic cassettes are denoted by combinations of number "16" and subdivision codes such as alphabets "A" to "D". In a case in which the electronic cassettes 16A to 16D do not need to be distinguished from each other, the electronic cassettes are denoted by only number "16" without a subdivision such as an alphabet.

The camera 26 is an optical camera that captures a usage environment in which the electronic cassette 16 is used. The usage environment includes an imaging place in which the subject H is present and the periphery of the imaging place. For example, the camera 26 is attached to a housing of the X-ray source 13. The electronic cassette 16 located at the position of an imaging part of the subject H can be included in the field of view CV of the camera 26, similarly to the X-ray source 13.

The camera 26 outputs, for example, a camera image 76 (see FIG. 15) which is an optical image indicating a captured usage environment. The camera image 76 is, for example, a color image and is a motion picture. The camera 26 includes a charge coupled device (CCD) image sensor or a complementary metal-oxide-semiconductor (CMOS) image sensor and outputs the captured camera image 76 as digital data. The camera 26 is connected to a network, such as a local area network (LAN) which is a wired network or a wireless network, and transmits the camera image 76 to the console 17 through the network. The camera 26 has a selection operation receiving function that receives an operation of selecting the electronic cassette 16 used for X-ray imaging without using an operation screen of the console 17, which will be described below. The camera image 76 is used in a case in which the selection operation receiving function is performed. The camera 26 is provided with an indicator 26A. The indicator 26A is, for example, a lamp. For example, the indicator 26A is used to issue various warnings in a case in which the function of receiving the operation of selecting the electronic cassette 16 is performed.

The X-ray source 13 includes an X-ray tube 13a that emits X-rays and an irradiation field limiter (collimator) 13b that limits the irradiation field of the X-rays emitted from the X-ray tube 13a. In this example, the X-ray source 13 is a fixed type that is fixed to the ceiling of the imaging room. The position of the X-ray source 13 in the horizontal direction can be moved by an overhead traveling device (not illustrated) and the height of the X-ray source 13 is adjusted by expanding or contracting a support 13c of the X-ray source 13.

The X-ray tube 13a includes a filament that emits thermal electrons and a target that collides with the thermal electrons emitted from the filament and emits X-rays. The irradiation field limiter 13b has, for example, a structure in which four lead plates that shield X-rays are provided on each side of a rectangle and a rectangular irradiation opening which transmits X-rays is provided at the center. The irradiation field limiter 13b moves the positions of the lead plates to change the size of the irradiation opening, thereby limiting the irradiation field.

The radiation source control device 14 includes a high voltage generator that supplies a high voltage to the X-ray source 13 and a controller that controls a tube voltage for determining an energy spectrum of the X-rays emitted from the X-ray source 13, a tube current for determining the amount of radiation emitted per unit time, and an X-ray emission time. The high voltage generator increases an input voltage using a transformer to generate a high tube voltage and supplies driving power to the X-ray source 13 through a high-voltage cable. The irradiation conditions, such as the tube voltage, the tube current, and the irradiation time, are manually set by the operator OP through an operation panel of the radiation source control device 14. In addition, the irradiation conditions are set by communication with the X-ray imaging apparatus 12.

An irradiation switch 23 is connected to the radiation source control device 14 through a signal cable. The irradiation switch 23 is operated by the operator OP. The irradiation switch 23 is pressed in two stages. In a case in which the irradiation switch 23 is pressed to the first stage, the radiation source control device 14 starts to warm up the X-ray source 13. In a case in which the irradiation switch 23 is pressed to the second stage, the radiation source control device 14 directs the X-ray source 13 to start to emit X-rays. The radiation source control device 14 includes a timer and operates the timer to measure the X-ray irradiation time. In a case in which the irradiation time set in the irradiation conditions elapses, the radiation source control device 14 stops the emission of X-rays.

Figure 2:
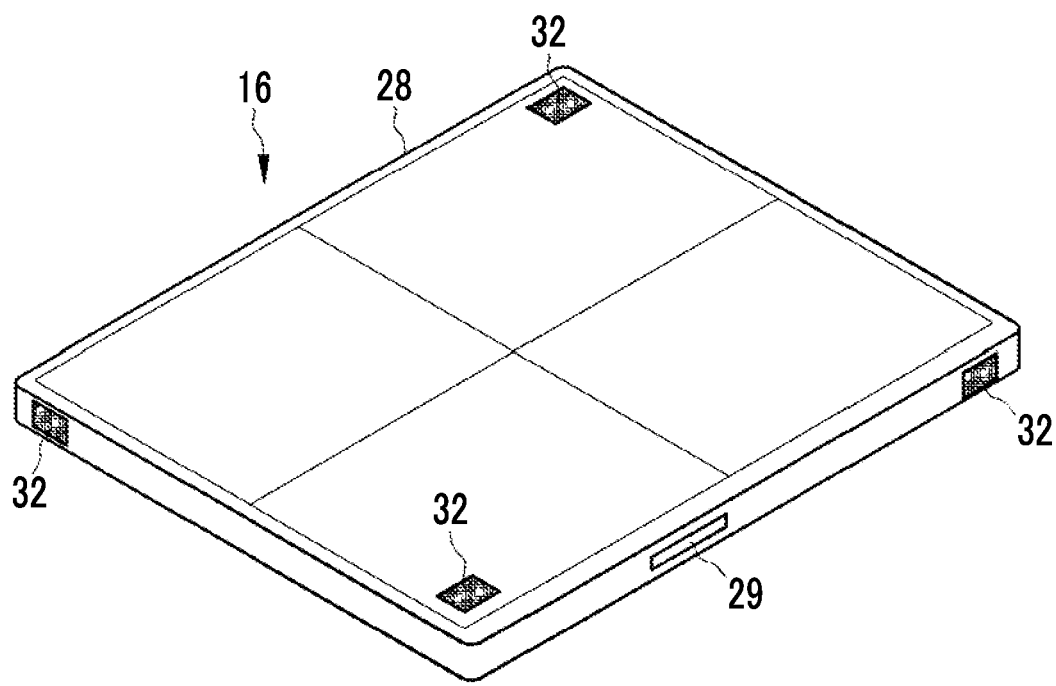
FIG. 2 is a perspective view illustrating a front surface side of an electronic cassette.
Figure 3:
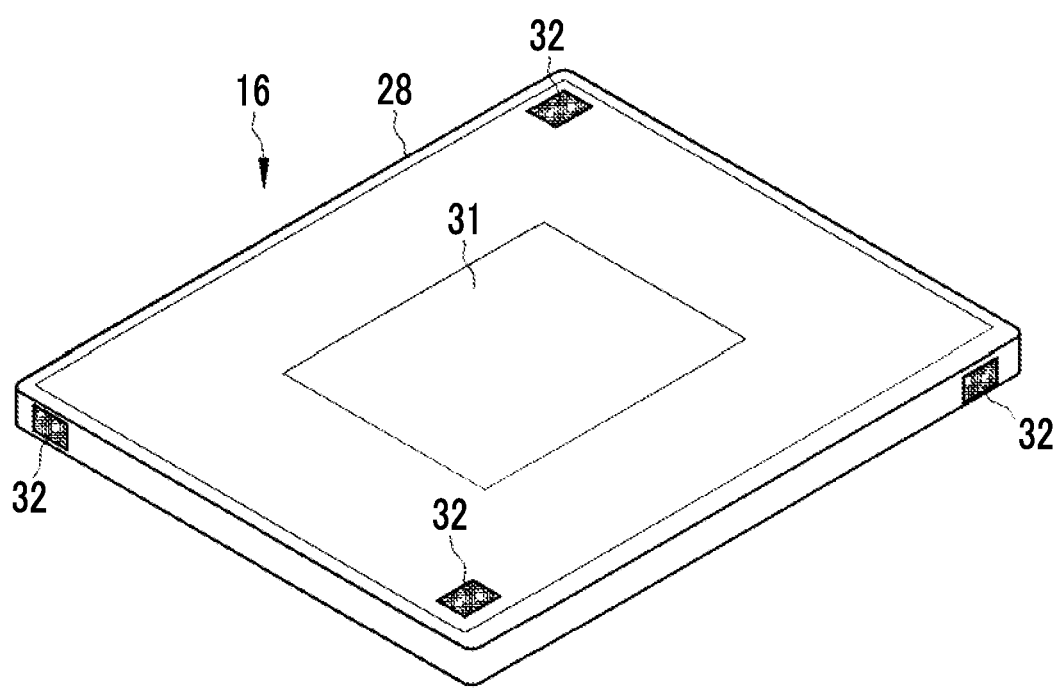
FIG. 3 is a perspective view illustrating a rear surface side of the electronic cassette.

As illustrated in FIGS. 2 and 3, the electronic cassette 16 includes a sensor panel (not illustrated) and a housing 28 that accommodates the sensor panel. The electronic cassette 16 is a portable X-ray image detection device which receives X-rays which have been emitted from the X-ray source 13 and then transmitted through the subject H and detects an X-ray image of the subject H based on the X-rays.

The sensor panel includes, for example, a scintillator and an optical detection substrate. The scintillator is a phosphor that converts X-rays into visible light. The optical detection substrate is a substrate in which a plurality of pixels that convert the visible light emitted from the scintillator into an electric signal and accumulate charge are two-dimensionally arranged. In addition, a direct-conversion-type sensor panel that directly converts X-rays into charge, without using a scintillator, may be used.

The electronic cassette 16 performs an image detection operation of detecting an X-ray image in synchronization with the emission of the X-rays from the X-ray source 13. As a synchronization method, a control signal for controlling an operation time is transmitted between the electronic cassette 16 and the X-ray generation apparatus 11 through the console 17 by communication to control the operation time. Alternatively, in a case in which the electronic cassette 16 has an irradiation start detection function of automatically detecting the start of the emission of X-rays, the irradiation start detection function is used to control the operation time. In a case in which the irradiation start detection function is used, the transmission of the control signal between the electronic cassette 16 and the X-ray generation apparatus 11 by communication is not required.

The housing 28 is, for example, made of stainless steel and a transmission plate that transmits X-rays is provided on a front surface of the housing 28 illustrated in FIG. 2. The housing 28 is a flat plate and has a substantially rectangular shape in a plan view. The electronic cassette 16 is a wireless type that can wirelessly communicate with the console 17. A communication unit 29 that communicates with the console 17 is provided in the housing 28 of the electronic cassette 16. The communication unit 29 includes a wired communication unit using a communication cable and a wireless communication unit that performs communication with radio waves.

As illustrated in FIG. 3, a battery 31 that supplies power to the sensor panel or the communication unit 29 is provided on a rear surface of the electronic cassette 16. The electronic cassette 16 can be driven by a battery in addition to a commercial power supply using a power cable.

Cassette identification data (ID) which is identification information for identifying the electronic cassette 16 is recorded on a memory (not illustrated) provided in the electronic cassette 16. The cassette ID is uniquely allocated to each electronic cassette 16. The cassette ID includes, for example, a character string including symbols or numbers. In a case in which the console 17 and the electronic cassette 16 communicate with each other, the cassette ID is added to communication data. In a case in which the console 17 transmits a control signal to the electronic cassette 16, the console 17 adds the cassette ID to the control signal to specify the electronic cassette 16 which is a transmission destination. In addition, in a case in which the console 17 receives an X-ray image from the electronic cassette 16, the console 17 reads the cassette ID from the accessory information of the X-ray image and specifies the electronic cassette 16 which is the transmission source of the X-ray image.

A plurality of ID markers 32 are provided on an outer surface of the housing 28. The cassette ID is recorded on the ID marker 32. The cassette ID is the same as the cassette ID recorded on the memory (not illustrated) of the electronic cassette 16. In the X-ray imaging system 10, the cassette ID recorded on the ID marker 32 is used for the function of receiving the operation of selecting the electronic cassette 16 using the camera image 76, which will be described below.

For example, the cassette ID is recorded in the form of a one-dimensional bar code or a two-dimensional bar code on the ID marker 32. A character string of the cassette ID may be recorded without any change. The ID marker 32 is provided on the outer surface of the housing 28 such that it can be recognized in the camera image 76. In this example, two ID markers 32 are provided on a diagonal line in each of the front surface of the housing 28 on which X-rays are incident and the rear surface opposite to the front surface. In addition, one ID marker 32 is provided on each of four side surfaces. Since the ID markers 32 are provided at a plurality of positions of the housing 28, the ID markers 32 are likely to be included in the camera image 76. Therefore, the probability that the ID markers 32 will be detected from the camera image 76 increases.

Here, the outer surface of the housing 28 includes the front and rear surfaces of the housing 28 and the side surfaces connected to both the front surface and the rear surface. At least a portion of the side surface may be curved. In addition, the side surfaces and the front and rear surfaces may be connected to each other, without a chamfer or a seam at the boundaries therebetween. In a case in which the ID marker 32 is provided on the front surface of the housing 28, it is preferable to dispose the ID marker 32 outside an imaging region in order to prevent the ID marker 32 from being included in the X-ray image. The ID marker 32 may be provided in the imaging region. In this case, it is preferable that the ID marker 32 is made of a material that is not included in the X-ray image.

The imaging region of the electronic cassette 16 has various sizes, such as a 14×17 rectangular size, a 17×17 square size, and a 10×12 rectangular size. In FIG. 1, for example, the electronic cassettes 16A and 16C are a 14×17 type, the electronic cassette 16B is a 10×12 type, and the electronic cassette 16D is a 17×17 type. The electronic cassettes 16A to 16D with different sizes are used for the purpose.

Some electronic cassettes 16 are used for free imaging as illustrated in FIG. 1 and some electronic cassettes 16 are placed on an upright imaging stand or a decubitus imaging stand and are then used. In general, a plurality of different electronic cassettes 16 that are used for various purposes are present in the imaging room.

In a case in which the electronic cassette 16 is used for imaging, the electronic cassette 16 needs to communicate with the console 17, unlike a film cassette or an imaging plate (IP) cassette. Therefore, the operator OP selects the electronic cassette 16 to be used for X-ray imaging as a use cassette before performing X-ray imaging. The use cassette is selected by the console 17. As described above, in a case in which the use cassette is selected, the console 17 communicates with the selected use cassette to transmit various kinds of control information to the use cassette or to receive the X-ray image from the use cassette. The operation of the console 17 selecting the use cassette is referred to as, for example, pairing.

The operator OP performs a positioning operation of positioning the electronic cassette 16 with respect to the subject H during X-ray imaging. At that time, in a case in which the electronic cassette 16 and the console 17 are not paired, it is necessary to move the console 17 to a certain place and to directly operate the console 17 for pairing. In the X-ray imaging system 10, the console 17 detects the electronic cassette 16 close to the subject H through the camera image 76 and receives the operation of the operator OP selecting the electronic cassette 16 to be used for X-ray imaging. The ID marker 32 is used for the function of receiving the operation of selecting the electronic cassette 16.

Figure 4:
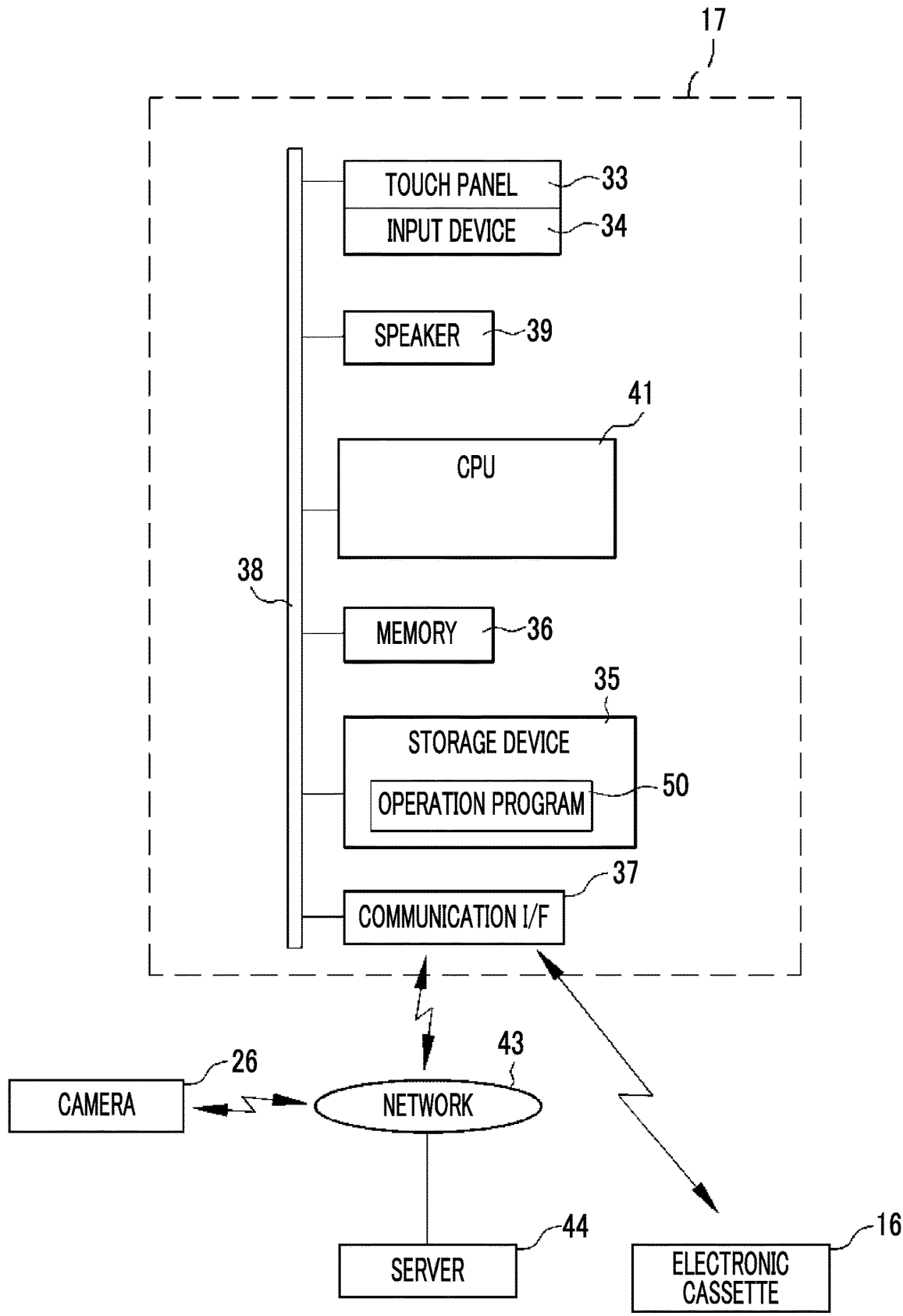
FIG. 4 is a block diagram schematically illustrating the electrical configuration of a console.

In FIG. 4, the console 17 is implemented by installing, for example, an operation program 50 for a console in a notebook personal computer. The console 17 includes a touch panel 33, an input device 34, a storage device 35, a memory 36, a central processing unit (CPU) 41, a communication interface (I/F) 37, and a speaker 39. These units are connected to each other through a data bus 38. The touch panel 33 functions as an input device that receives an operation command input by a touch operation and functions as a display unit that displays various kinds of information.

The storage device 35 is, for example, a hard disk drive provided in the console 17. In addition, the storage device 35 may be an external device or a network storage that can be accessed through a network 43. The storage device 35 stores a control program, such as an operating system, various application programs, and various kinds of data associated with the programs. The application programs include the operation program 50 that causes a notebook personal computer to function as the console 17.

The memory 36 is a work memory that is used by the CPU 41 to perform processes. The CPU 41 loads a program stored in the storage device 35 to the memory 36 and executes a process based on the program to control the overall operation of each unit of the console 17. The communication I/F 37 performs communication with the electronic cassette 16 or a network 43. The network 43 is, for example, a LAN installed in a hospital including the imaging room. The console 17 is connected to various servers 44 and the camera 26 in the hospital through the network 43 so as to communicate therewith. The console 17 receives the camera image 76 from the camera 26 through the network 43 and receives an X-ray imaging order from the server 44. The speaker 39 is used to notify warning sounds or warning messages required for the console 17 to perform processes.

The basic functions of the console 17 will be described with reference to FIGS. 5 to 12. The basic functions of the console 17 include, for example, a display function of displaying the imaging order or the X-ray image received from the electronic cassette 16 on the touch panel 33 which is a display unit, an image processing function of processing the X-ray image, and a cassette control function of controlling the electronic cassette 16.

Figure 5:
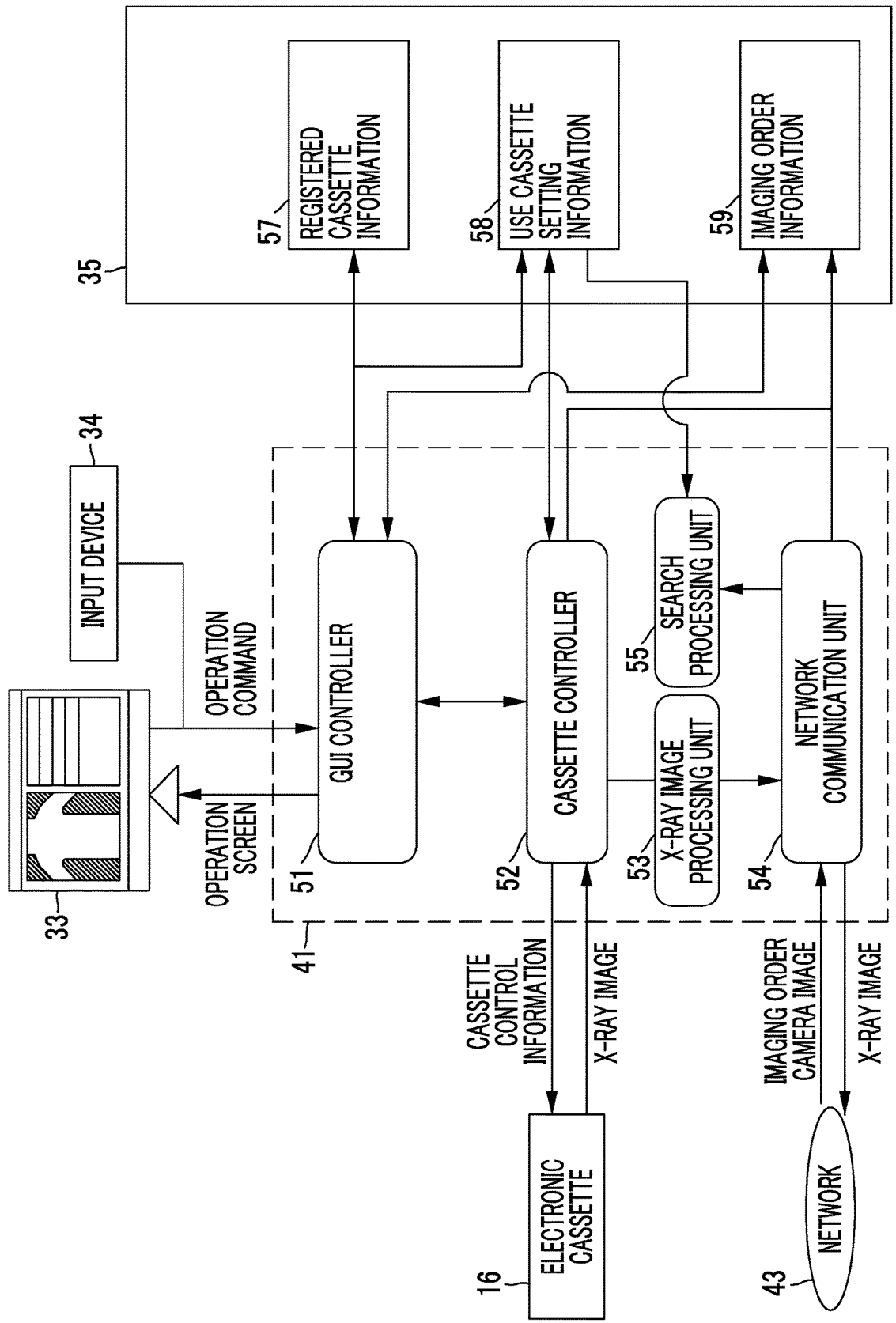
FIG. 5 is a functional block diagram illustrating each unit for implementing the basic function of the console.

As illustrated in FIG. 5, in a case in which the operation program 50 is run, the CPU 41 functions as a graphical user interface (GUI) controller 51, a cassette controller 52, an X-ray image processing unit 53, a network communication unit 54, and a search processing unit 55 in cooperation with the memory 36. The GUI controller 51 is a display controller that performs control for displaying various kinds of information, such as the X-ray image captured by the electronic cassette 16 and an operation screen generated by a GUI, on the touch panel 33. In addition, the GUI controller 51 functions as an input controller that receives operation commands input from the input device 34 or the touch panel 33 in cooperation with the operation screen.

Figure 9:
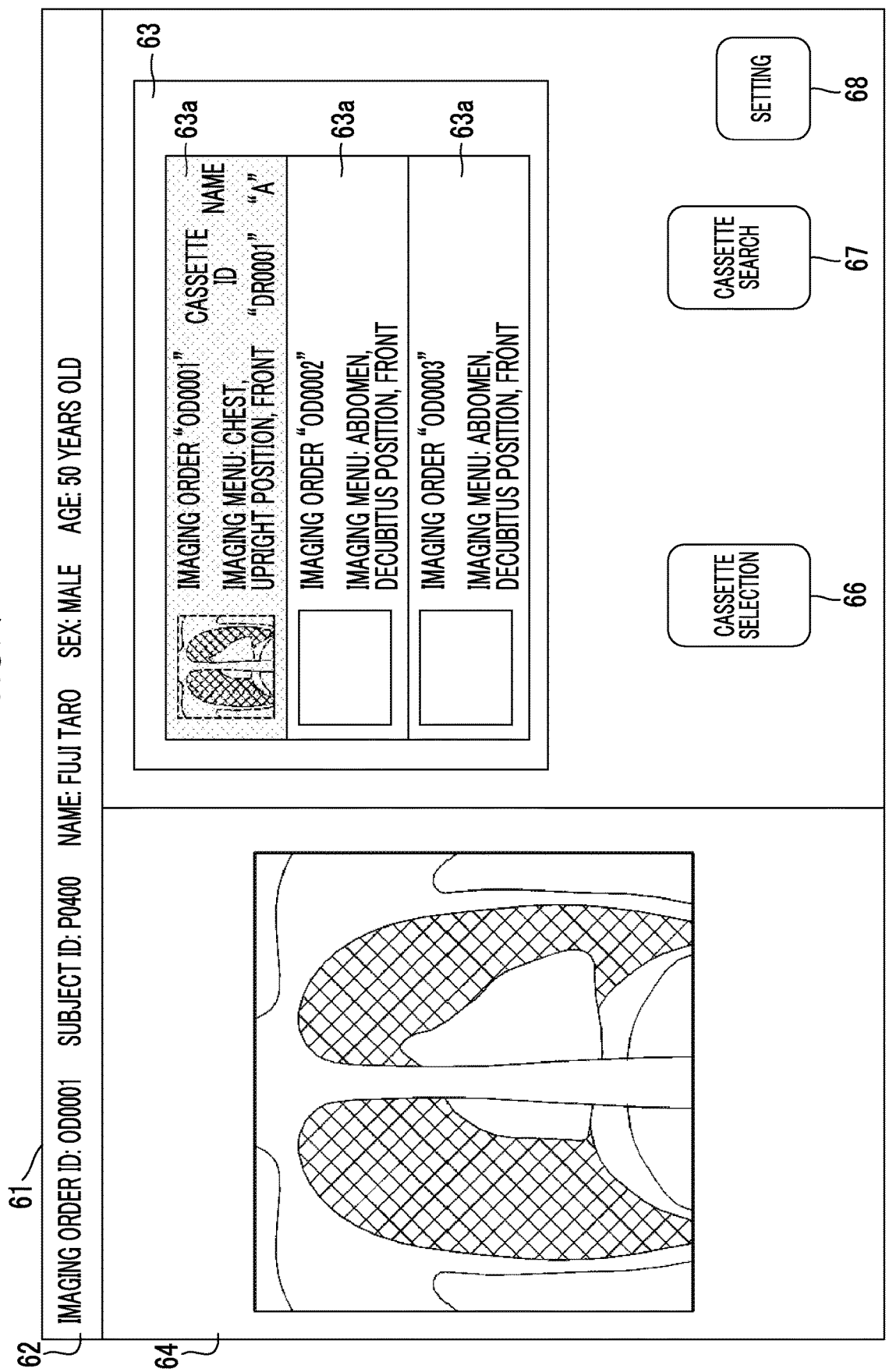
FIG. 9 is a diagram illustrating an imaging order display screen.
Figure 10:
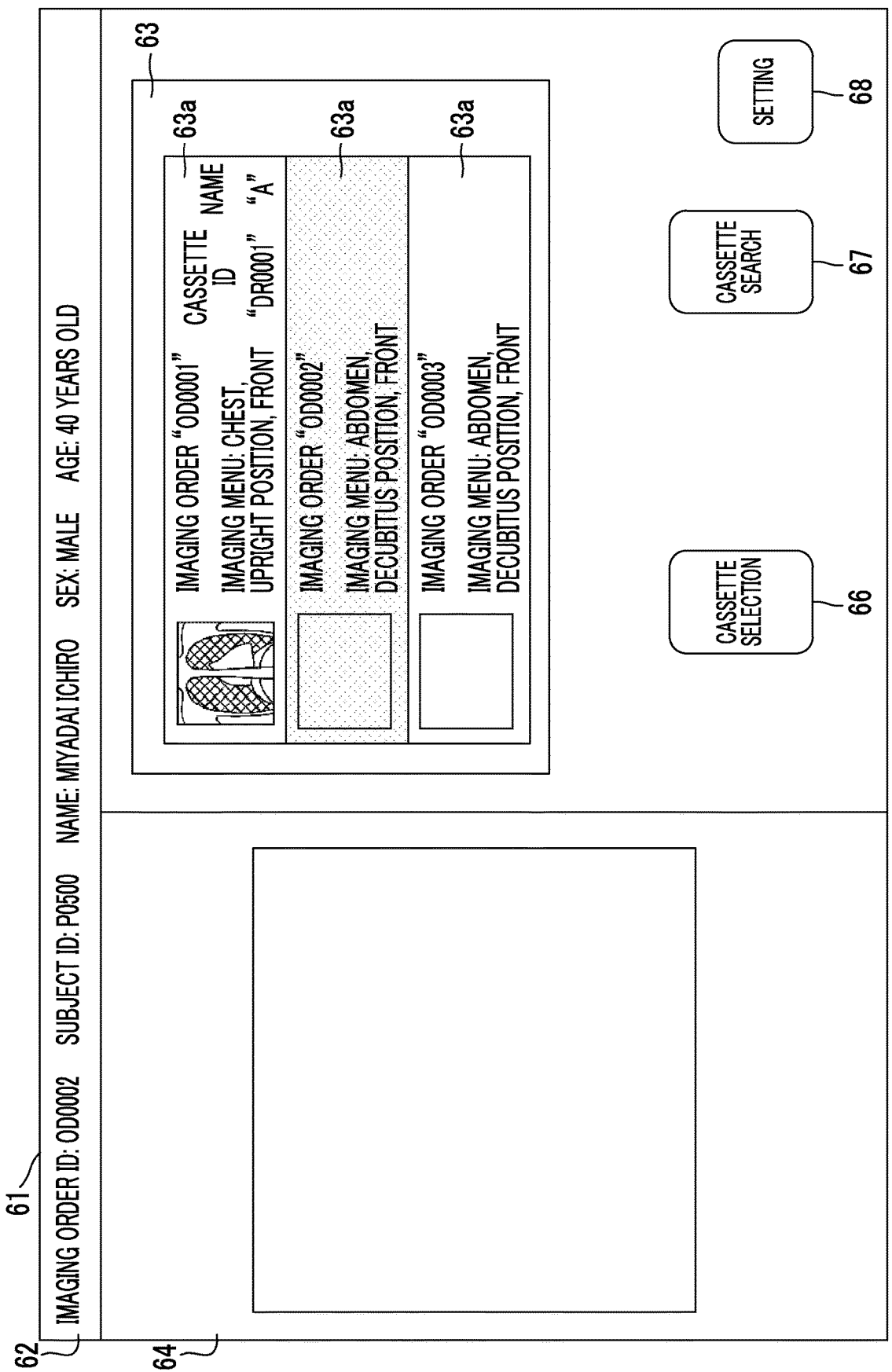
FIG. 10 is a diagram illustrating another example of the imaging order display screen.

The storage device 35 stores the information of the operation screen illustrated in, for example, FIG. 9 or FIG. 10. The GUI controller 51 accesses the storage device 35, reads the information of the operation screen, and generates an operation screen to be output to the touch panel 33.

The cassette controller 52 communicates with the electronic cassette 16 through the communication I/F 37 to control the electronic cassette 16. The cassette controller 52 transmits a command to turn on or off the electronic cassette 16, a command to switch the mode to a power saving mode and an imaging preparation state (ready status), and various kinds of cassette control information, such as the irradiation conditions, received from the GUI controller 51 to the electronic cassette 16.

A plurality of electronic cassettes 16 that can be controlled by the console 17 are registered in the console 17 in advance. The registration information is stored as registered cassette information 57 in the storage device 35. As illustrated in FIG. 6, a cassette ID, a name, a plane size, a communication address, and specification information are recorded in the registered cassette information 57. The specification information includes, for example, the correction information of each electronic cassette 16 used to correct the X-ray image. In addition, the specification information includes information related to an imaging part and an imaging procedure suitable for each electronic cassette 16. In the registered cassette information 57, the plane size is recorded as an item different from the specification information. However, the plane size is also included in the specification information. The specification information including the plane size of the electronic cassette 16 or the information related to, for example, the imaging procedure can be used to determine suitability for the imaging order.

The correction information includes, for example, offset data used to correct a dark current and defective pixel data related to the defects of pixels in the sensor panel. In the registered cassette information 57 illustrated in FIG. 6, five electronic cassettes 16 with cassette IDs "DR0001" to "DR0005" are registered. Cassettes A to D corresponding to the cassette IDs "DR0001" to "DR0004" correspond to the electronic cassettes 16A to 16D, respectively. The use cassette used for X-ray imaging is selected from the registered cassettes which are the electronic cassettes 16 registered in the registered cassette information 57.

The information of the electronic cassette 16 which has been selected from the registered cassettes by the operator OP and then set as the use cassette by the console 17 is recorded in the use cassette setting information 58 illustrated in FIG. 7. The use cassette setting information 58 includes a setting information item, a status item, an imaging order item, in addition to a cassette ID and a name which are the same as those in the registered cassette information 57. The setting information is information indicating whether the electronic cassette has been set as the use cassette. In a case in which the electronic cassette has been set as the use cassette, "set" is written in the setting information item. In a case in which the electronic cassette has not been set as the use cassette, "unset" is written in the setting information item.

Status information indicating the operating state of the electronic cassette 16 which has been set as the use cassette is recorded in the status item. Examples of the status include a ready status in which preparation for imaging has been completed and a sleep status in which the electronic cassette is on standby and is in a power saving mode. In a case in which the use cassette has been set, the cassette controller 52 communicates with the electronic cassette 16 set as the use cassette and monitors the status of the use cassette. Then, the cassette controller 52 records the status information of the use cassette in the use cassette setting information 58. The cassette controller 52 controls the status of the use cassette and updates the status information at any time with a change in the status of the use cassette.

The imaging order item indicates an imaging order corresponding to the X-ray imaging performed using the use cassette. An order ID of the imaging order corresponding to the use cassette is recorded in the imaging order item (see FIG. 12). In a case in which the X-ray imaging using the use cassette has been completed, the information of the imaging order in the use cassette setting information 58 is cleared. FIG. 7 illustrates a state in which no electronic cassettes 16 are set as the use cassette.

FIG. 8 illustrates an example of imaging order information 59. The imaging order is, for example, imaging request information that is issued from a diagnosis and treatment department, such as a surgery department or an internal department in which X-ray imaging is performed, to a radiology department and includes items such as an order ID, a subject ID (patient ID), and an imaging menu. The imaging menu includes an imaging part, such as the chest or the abdomen, an imaging posture, such as an upright position or a decubitus position, and information for designating the imaging procedure of X-ray imaging including an imaging direction, such as the front or the rear.

In addition to the above-mentioned items, a subject information item (not illustrated) indicating the name, sex, age, height, and weight of the subject H is included in the imaging order information 59. In addition, the imaging order information 59 includes items, such as a diagnosis and treatment department to which a person who requests imaging belongs, the ID of the person who requests imaging, a receiving date and time, the purpose of imaging, such as the monitoring of conditions after the surgery or the determination of the effect of treatment remedies, and orders issued from the person who requests imaging to the operator OP.

In addition, the imaging order information 59 includes a completion information item and a use cassette item for each imaging order. The completion information is information about whether X-ray imaging has been completed. In a case in which imaging has been completed, "imaging completed" is registered in the completion information item. In a case in which imaging has not been completed, "uncompleted" is recorded in the completion information item. The cassette ID of the use cassette used for X-ray imaging is recorded in the use cassette item. In this example, for an imaging order "OD0001", imaging has been completed and the cassette ID "DR0001" of the use cassette is recorded.

The console 17 acquires the imaging order from the server 44 that forms a hospital information system (HIS) or a radiation information system (RIS) and registers the imaging order in the imaging order information 59. In addition, the imaging order may be directly input by the operator OP through the console 17 and then registered, instead of being acquired from the server 44. In a case in which X-ray imaging for each imaging order has been completed, the data of the X-ray images corresponding to each imaging order is recorded in the imaging order information 59 so as to be associated with each imaging order.

Returning to FIG. 5, the cassette controller 52 specifies the cassette ID of the use cassette with reference to the use cassette setting information 58 and communicates with the specified use cassette. The cassette controller 52 receives the data of the X-ray image from the use cassette and transmits the received X-ray image to the X-ray image processing unit 53. As described above, for example, the cassette controller 52 controls or monitors the status of the use cassette.

The X-ray image processing unit 53 performs various types of image processing, such as offset correction, defect correction, sharpness correction, and frequency processing, for the X-ray image. Instead of the console 17, the electronic cassette 16 may perform some of the various types of image processing for the X-ray image, for example, offset correction and defect correction. The X-ray image subjected to the image processing in the X-ray image processing unit 53 is stored in, for example, the storage device 35 of the console 17, is transmitted to an image storage server, such as a picture archiving and communication system (PACS) server, and is then stored in the server.

The network communication unit 54 communicates with the server 44 through the communication I/F 37 and the network 43 and receives the imaging order from the RIS or the HIS or transmits the X-ray image to the image storage server such as a picture archiving and communication system (PACS) server. In addition, the network communication unit 54 functions as a camera image acquisition unit that acquires the camera image 76 from the camera 26. The functions of the search processing unit 55 will be described below.

An imaging order display screen 61 and a use cassette selection operation using an operation screen will be described with reference to FIGS. 9 to 12. The imaging order display screen 61 illustrated in FIGS. 9 and 10 is an operation screen that is output to the touch panel 33 by the GUI controller 51.

The imaging order display screen 61 includes a patient information display region 62 in which patient information including the ID of the imaging order and the name, ID, sex, and age of a patient is displayed, an imaging order display region 63 in which the imaging orders registered in the console 17 are displayed, and an image display region 64 in which a captured X-ray image is displayed. A cassette selection button 66 for selecting the use cassette used for imaging from the registered cassettes is provided below the imaging order display region 63. Reference numeral 67 indicates a camera operation button for commanding the start and stop of the operation of the camera 26 and reference numeral 68 indicates a setting button for various settings.

In a case in which there are a plurality of imaging orders, the plurality of imaging orders are displayed in a list form in the imaging order display region 63. In this example, the imaging order display region 63 includes three imaging orders illustrated in FIG. 9. The imaging orders are displayed in the imaging order display region 63 on the basis of the imaging order information 59 illustrated in FIG. 8. Information for designating the imaging procedure of each imaging order, such as "the chest, an upright position, and the front" is displayed in each imaging order display field 63a of the imaging order display region 63.

In a case in which an operation of clicking a mouse of the input device 34 or a touch operation through the touch panel 33 is performed for one display field 63a, an imaging order corresponding to the display field 63a is designated. The display field 63a of the designated imaging order is highlighted (hatched) so as to be distinguished from the other imaging orders which are not designated. This example shows a state in which the imaging order "OD0001" is designated.

A thumbnail image which is a minified image of the captured image is displayed at the left end of the display field 63a corresponding to the processed (captured) imaging order. No thumbnail images are displayed in the display fields 63a corresponding to the unprocessed imaging orders. This example shows a state in which the imaging order "OD0001" has been processed, a thumbnail image is displayed in the display field 63a corresponding to the processed imaging order, the other two imaging orders have not been processed, and no thumbnail images are displayed in the display fields 63a corresponding to the unprocessed imaging orders.

A captured X-ray image of the imaging order selected in the imaging order display region 63 is displayed in the image display region 64. In this example, an X-ray image corresponding to the imaging order "OD0001" is displayed. Of course, an image selected from a plurality of captured X-ray images may be displayed in the image display region 64.

For example, a selection operation (also referred to as a pairing operation) of selecting the electronic cassette 16 to be used for X-ray imaging corresponding to the unprocessed imaging order is performed as follows. First, as illustrated in FIG. 10, an unprocessed imaging order "OD0002" is selected in the imaging order display region 63. In this state, in a case in which the cassette selection button 66 is operated, as illustrated in (A) and (B) of FIG. 11, a use cassette selection screen 69 is displayed on the touch panel 33. The registered cassette information 57 is displayed on the use cassette selection screen 69.

The operator OP determines which of the electronic cassettes 16 is suitable for X-ray imaging corresponding to the imaging order on the basis of the content of the imaging order and selects an electronic cassette 16 to be used for X-ray imaging from the registered cassettes. The selection operation is performed by a touch operation or a mouse click operation. (A) of FIG. 11 illustrates a state in which a cassette C with a cassette ID "DR0003" is selected as represented by hatching. In a case in which the selection operation is performed in this way, the console 17 sets the selected electronic cassette 16 as the use cassette and updates the use cassette setting information 58.

In a case in which the use cassette is set as illustrated in (B) of FIG. 11, the cassette ID ("DR0003") and name "C" of the set use cassette are displayed in the display field 63a of the imaging order display region 63.

In a case in which the use cassette is set as illustrated in FIG. 12, the use cassette is associated between the registered cassette information 57 and the use cassette setting information 58. The order ID ("OD0002") is registered for the set use cassette in the use cassette setting information 58 and is associated between the use cassette setting information 58 and the imaging order information 59.

Here, in order to distinguish the cassette ID recorded on the memory of the electronic cassette 16 or the ID marker 32 from the cassette ID of the cassette registered in the console 17, the cassette ID recorded on the memory of the electronic cassette 16 or the ID marker 32 is referred to as a first cassette ID and the cassette ID of the registered cassette is referred to as a second cassette ID. The first cassette ID corresponds to identification information and a cassette ID in the claims. In addition, the registered cassette information 57 corresponds to registration information of a registered cassette in the claims and the second cassette ID included in the registration information.

Figure 13:
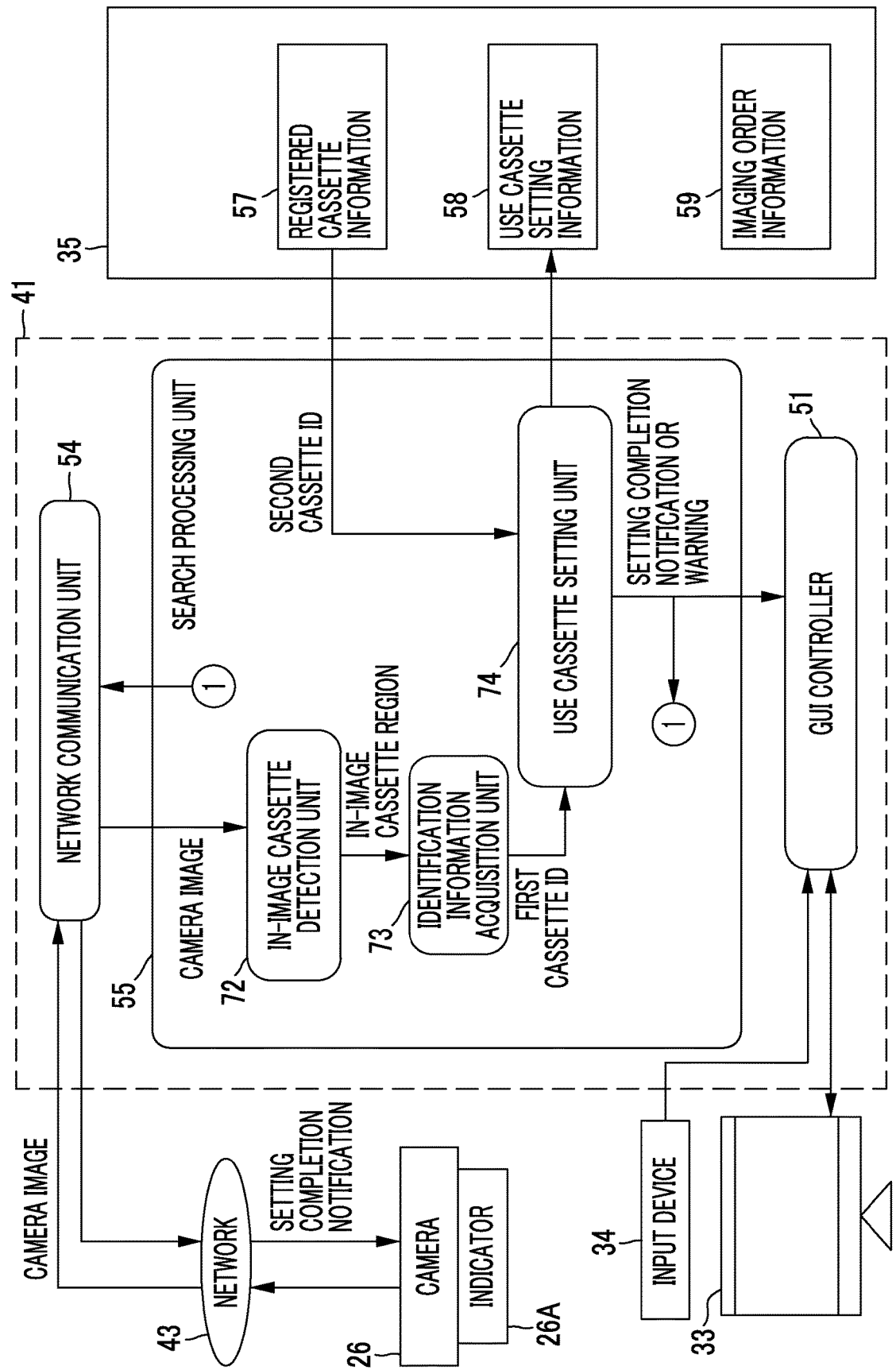
FIG. 13 is a functional block diagram illustrating each unit for implementing an electronic cassette selection operation receiving function.

The function of the console 17 receiving the operation of selecting the electronic cassette 16 using the camera 26 will be described with reference to FIGS. 13 to 17. Specifically, the function of receiving the operation of selecting the electronic cassette 16 is the function of the console 17 receiving the operation of the operator OP selecting the electronic cassette 16 to be used for X-ray imaging through the camera 26. In FIG. 13, the network communication unit 54 acquires the camera image 76 captured by the camera 26 through the network 43. The camera image 76 is input to the search processing unit 55.

Figure 14:
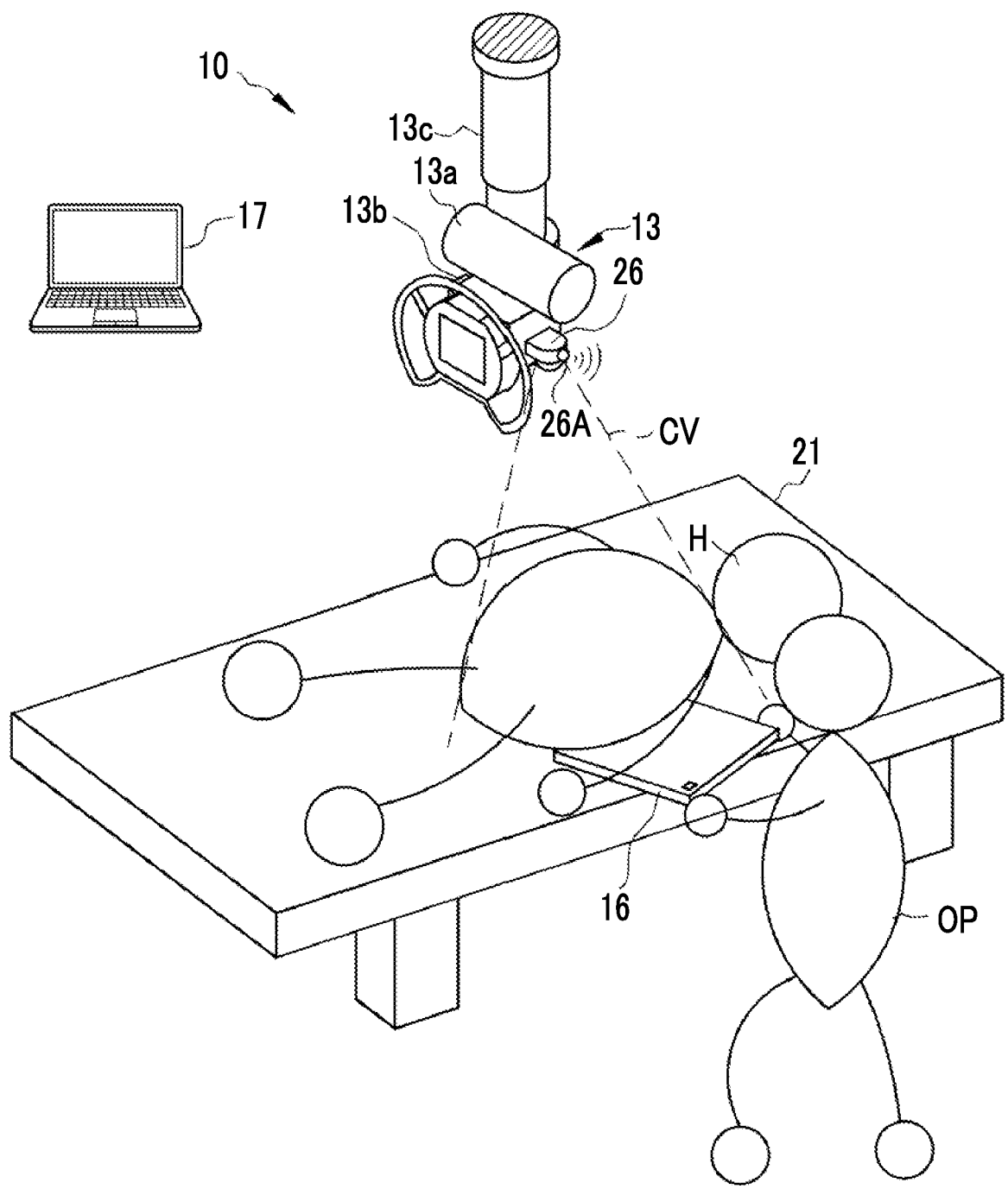
FIG. 14 is a diagram illustrating an environment in which the electronic cassette is used.

FIGS. 14 and 15 are diagrams illustrating the camera image 76 captured by the camera 26. For example, as illustrated in FIG. 14, during X-ray imaging, the operator OP stands next to the subject H and positions the subject H and the X-ray source 13 such that the subject H faces the X-ray source 13 or relatively positions the subject H and the electronic cassette 16. The camera 26 captures the usage environment of the X-ray imaging performed using the electronic cassette 16. In this example, since the camera 26 is provided in the X-ray source 13, the field of view CV of the camera 26 includes the irradiation field of the X-ray source 13.

In a case in which the image of the chest or abdomen of the subject H is captured, the electronic cassette 16 is placed between the body of the subject H and the bed 21. The position where the electronic cassette 16 is placed corresponds to the irradiation field of the X-ray source 13. Therefore, in a state in which a portion of the electronic cassette 16 is inserted between the body of the subject H and the bed 21, the electronic cassette 16 is included in the field of view CV of the camera 26.

(A) of FIG. 15 illustrates an example of the camera image 76 obtained by capturing the aspect illustrated in FIG. 14. (A) of FIG. 15 illustrates an aspect in which the subject H is viewed from the position of the camera 26 provided above the subject H. The field of view CV of the camera 26 includes the electronic cassette 16 whose housing is partially inserted between the body of the subject H and the bed 21. (B) of FIG. 15 illustrates the camera image 76 obtained by capturing the aspect.

The camera 26 outputs the camera image 76 as a motion picture. Therefore, while the camera 26 captures an image, the camera image 76 obtained by capturing the aspect of the usage environment of the electronic cassette 16 is output to the search processing unit 55 of the console 17 in real time. The camera image 76 may be displayed on the touch panel 33 which is a display unit of the console 17 under the display control of the GUI controller 51.

The search processing unit 55 includes an in-image cassette detection unit 72, an identification information acquisition unit 73, and a use cassette setting unit 74.

Figure 16:
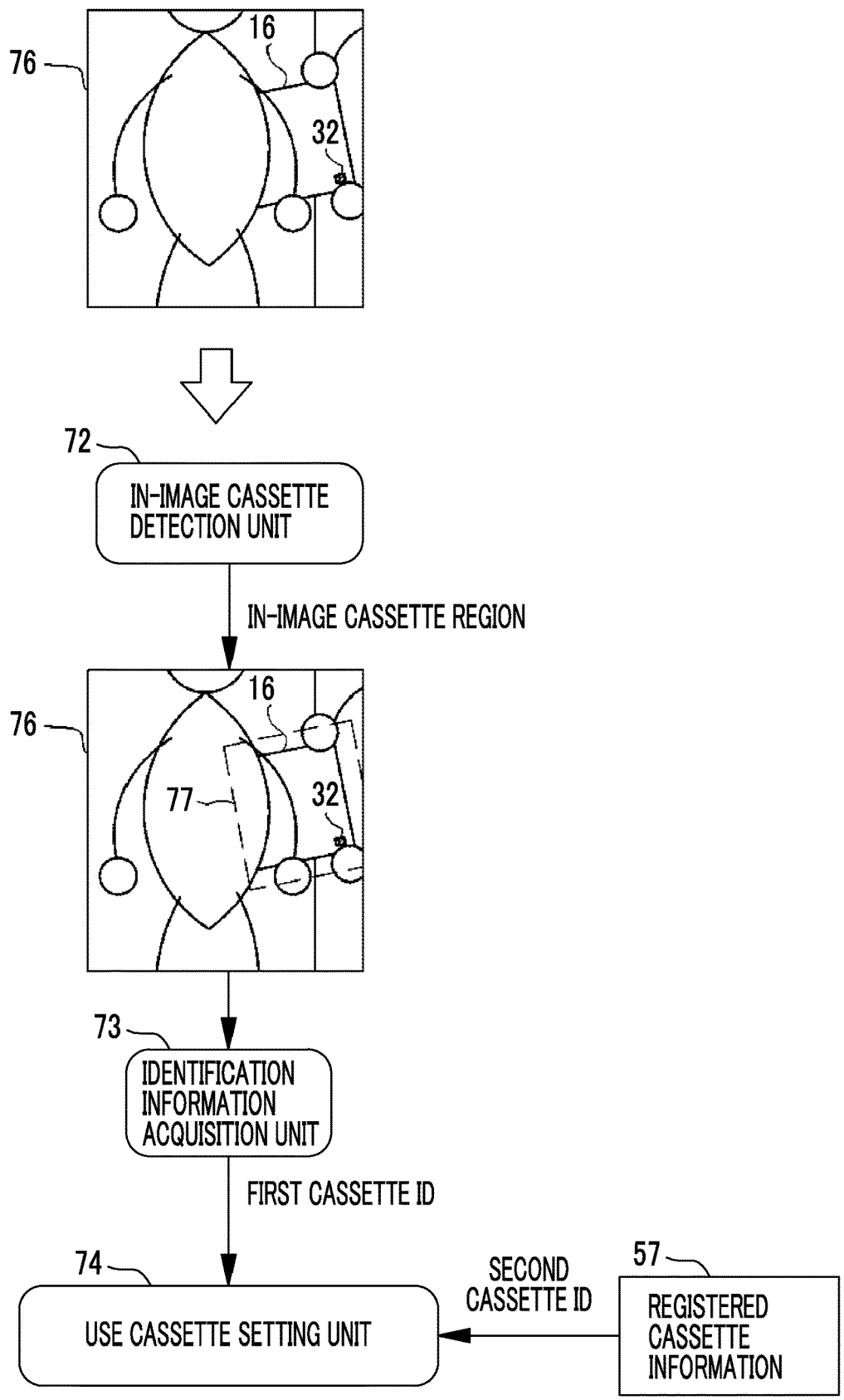
FIG. 16 is a diagram illustrating a process of acquiring a cassette ID from the camera image.

As illustrated in FIG. 16, the in-image cassette detection unit 72 detects an in-image cassette region 77 of the electronic cassette 16 included in the camera image 76 on the basis of the camera image 76. The in-image cassette detection unit 72 detects the electronic cassette 16 included in the camera image 76 on the basis of the camera image 76, using a known image recognition method such as pattern matching. For example, the in-image cassette detection unit 72 extracts a pattern, such as the contour of the electronic cassette 16 or the bed 21, as a feature amount from the camera image 76 and collates the extracted feature amount with the stored feature information including the contour of the electronic cassette 16. Contour information includes the planar shape of the electronic cassette 16 and the contour of the electronic cassette 16 as viewed from the side or an oblique direction. In a case in which there are features, such as colors, other than the contour of the electronic cassette 16, the collation may be performed using the feature amounts other than the contour.

The in-image cassette detection unit 72 detects a region including the detected position of the electronic cassette 16 and the periphery thereof as the in-image cassette region 77. Specifically, the in-image cassette region 77 is output as coordinate information in the camera image 76. The in-image cassette detection unit 72 outputs the detected in-image cassette region 77 as a detection result to the identification information acquisition unit 73.

The identification information acquisition unit 73 detects the ID marker 32 attached to the electronic cassette 16 from the in-image cassette region 77 on the basis of the camera image 76, using a known image recognition method such as pattern matching. Similarly to the detection of the electronic cassette 16, the ID marker 32 is detected by collating the stored feature amount of the ID marker 32 with the feature amount extracted from the camera image 76.

Then, the identification information acquisition unit 73 reads the first cassette ID from the detected ID marker 32. In this way, the identification information acquisition unit 73 acquires the first cassette ID which is identification information. The identification information acquisition unit 73 outputs the acquired first cassette ID and the information of the in-image cassette region 77 corresponding to the first cassette ID to the use cassette setting unit 74.

Figure 17:
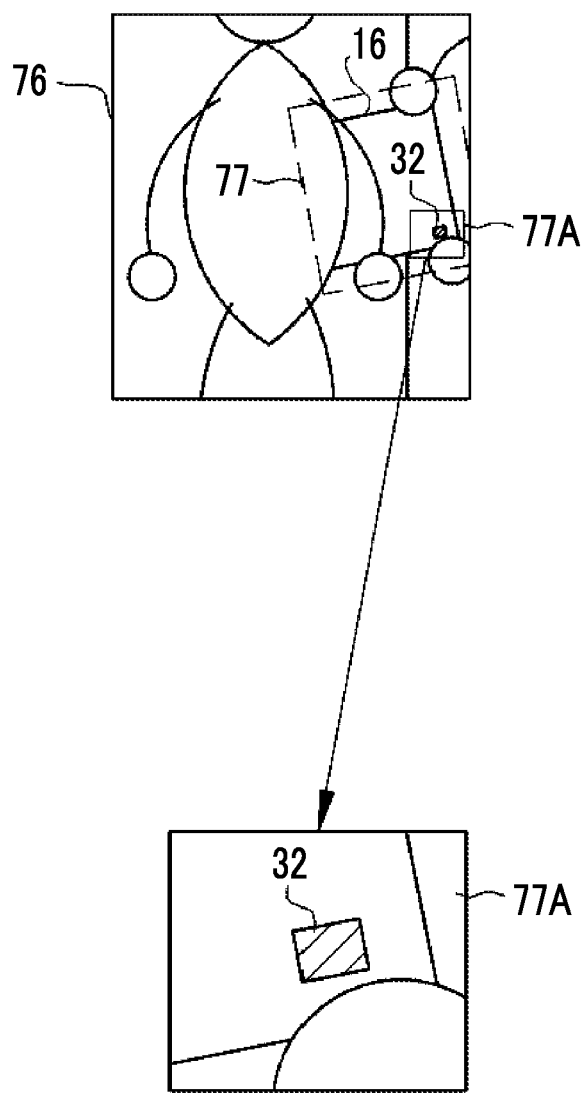
FIG. 17 is a diagram illustrating an aspect in which an ID marker portion is enlarged in the camera image.

In a case in which the first cassette ID is not read from the ID marker 32 at the standard magnification of the camera image 76, the identification information acquisition unit 73 enlarges a portion 77A including the ID marker 32 in the camera image 76 as illustrated in FIG. 17 and then reads the first cassette ID. The camera image 76 may be enlarged by electronic zooming. In a case in which the camera 26 has a zoom function, the search processing unit 55 transmits a zoom command to the camera 26 on the basis of the processing result of the identification information acquisition unit 73 to activate the zoom function.

In a case in which the first cassette ID is acquired, the use cassette setting unit 74 accesses the registered cassette information 57 and acquires the second cassette ID of the registered cassette. In a case in which the first cassette ID and the second cassette ID are acquired, the use cassette setting unit 74 collates the first cassette ID with the second cassette ID. The use cassette setting unit 74 corresponds to a collation unit. In a case in which a plurality of second cassette IDs are registered in the registered cassette information 57, the collation is performed for each second cassette ID. In a case in which the second cassette ID matched with the first cassette ID is found, the collation may end in that stage.

In a case in which the second cassette ID matched with the first cassette ID is found on the basis of the collation result, the use cassette setting unit 74 determines the electronic cassette 16 with the first cassette ID as the registered cassette. In a case in which the first cassette ID is not matched with any of the registered second cassette IDs, the use cassette setting unit 74 determines that the electronic cassette 16 in the camera image 76 is not the registered cassette. The use cassette setting unit 74 performs the above-mentioned determination to determine whether the electronic cassette 16 included in the camera image 76 is the registered cassette.

In a case in which the detected electronic cassette 16 is determined to be the registered cassette, the use cassette setting unit 74 performs a use cassette setting process of setting the electronic cassette 16 as the use cassette. In the use cassette setting process, the use cassette setting information 58 is updated by the same process as that performed by the cassette controller 52. In this way, pairing is performed between the console 17 and the use cassette selected as the electronic cassette 16 used for X-ray imaging.

As illustrated in FIG. 13, in a case in which the setting of the use cassette is completed, the use cassette setting unit 74 outputs a setting completion notification. The setting completion notification is displayed on the touch panel 33 through the GUI controller 51 and is also transmitted to the camera 26 through the network communication unit 54. In a case in which the setting completion notification is received, the camera 26 turns on the indicator 26A. The indicator 26A notifies the operator OP that the setting of the use cassette has been completed. The indicator 26A corresponds to a notification unit.

The use cassette setting unit 74 performs various warning processes. For example, the use cassette setting unit 74 issues a warning in a case in which the first cassette ID of the electronic cassette 16 in the camera image 76 is not capable of being acquired or in a case in which there are no registered cassettes. The warning process is performed through the touch panel 33 or the speaker 39 of the console 17 or the indicator 26A of the camera 26.

The camera 26 outputs the camera image 76 which is a motion picture in real time. The search processing unit 55 repeats the above-mentioned process while the camera image 76 is being output.

The operation of the above-mentioned configuration will be described with reference to the flowcharts illustrated in FIGS. 18 to 22. In a case in which the operator OP performs X-ray imaging using the electronic cassette 16, the operator OP selects the use cassette to be used for X-ray imaging from a plurality of electronic cassettes 16 according to the content of an imaging order.

In general, the use cassette is selected through the operation screen of the console 17 as illustrated in FIGS. 10 to 12. However, in some cases, the operator OP starts to position the electronic cassette 16 with respect to the subject H, without performing the selection operation. In this case, the function of receiving the operation of selecting the electronic cassette 16 using the camera 26 is used. In a case in which the selection operation receiving function is used, the camera operation button 67 (see FIG. 9) is operated in advance to start up the camera 26.

Figure 18:
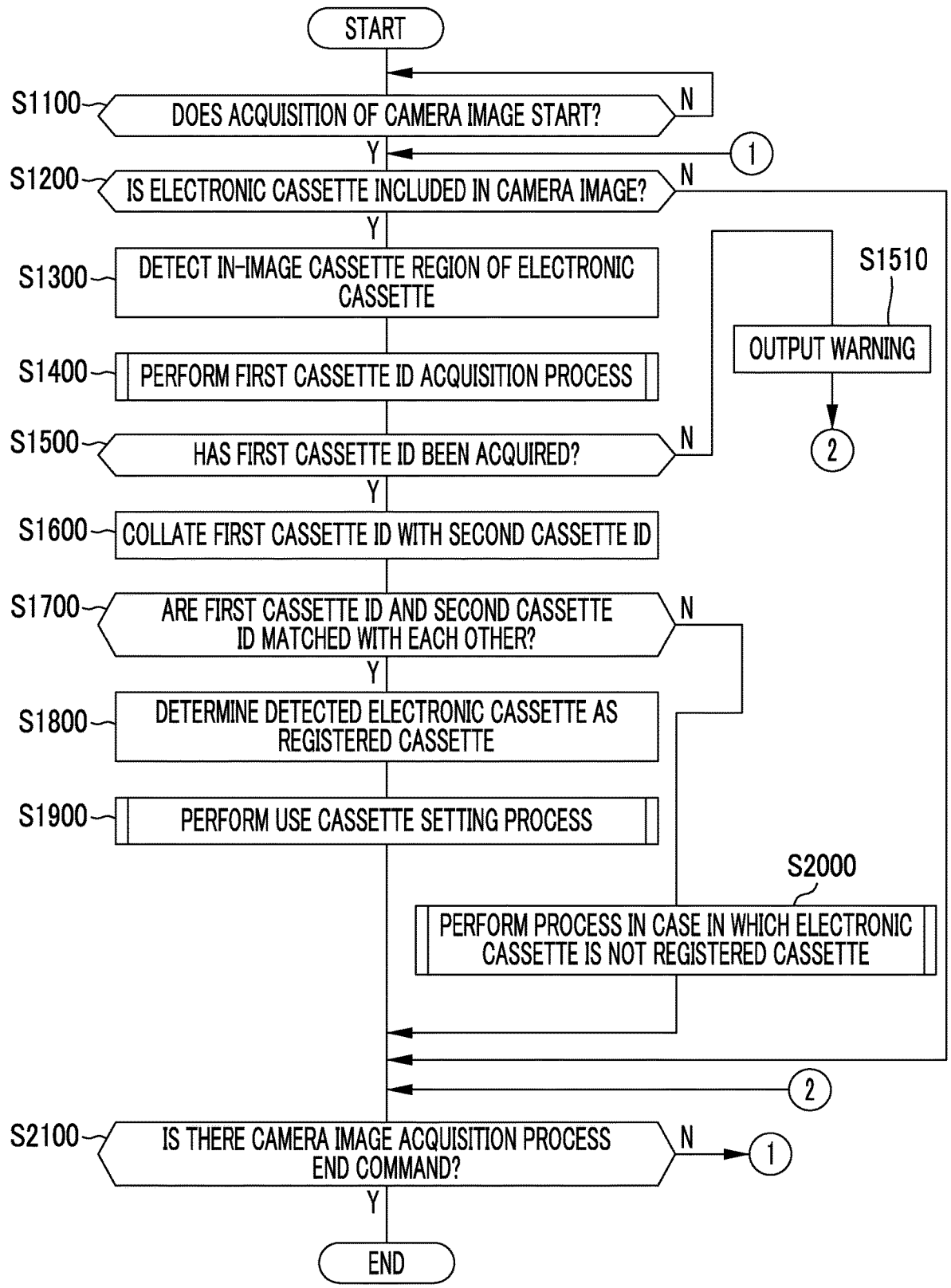
FIG. 18 is a flowchart illustrating the procedure of a selection operation receiving process.

As illustrated in FIG. 18, in a case in which the camera operation button 67 is operated, the camera 26 is operated to start the output of the camera image 76. Then, the network communication unit 54 starts to acquire the camera image 76 which is a motion picture output from the camera 26 in real time (Step S1100).

As illustrated in FIG. 14, during positioning, the operator OP stands next to the subject H and performs positioning such that the X-ray source 13 faces an imaging part (in this example, the chest) of the subject H. Then, the operator OP inserts a portion of the electronic cassette 16 between the subject H and the bed 21 in order to put the electronic cassette 16 on the imaging part of the subject H. The electronic cassette 16 is inserted into the field of view CV including the irradiation field of the X-ray source 13 by the above-mentioned operation and the electronic cassette 16 is included in the camera image 76. The camera image 76 is input to the in-image cassette detection unit 72 of the search processing unit 55.

The in-image cassette detection unit 72 performs an image recognition process on the basis of the camera image 76 and checks whether the electronic cassette 16 is included in the camera image 76 (S1200). In a case in which the electronic cassette 16 is included in the camera image 76 (Y in S1200), as illustrated in FIG. 16, the in-image cassette detection unit 72 detects the in-image cassette region 77 of the electronic cassette 16 (S1300). The in-image cassette detection unit 72 outputs the detected in-image cassette region 77 to the identification information acquisition unit 73.

In a case in which the in-image cassette region 77 is input from the in-image cassette detection unit 72, the identification information acquisition unit 73 performs a first cassette ID acquisition process (S1400).

Figure 19:
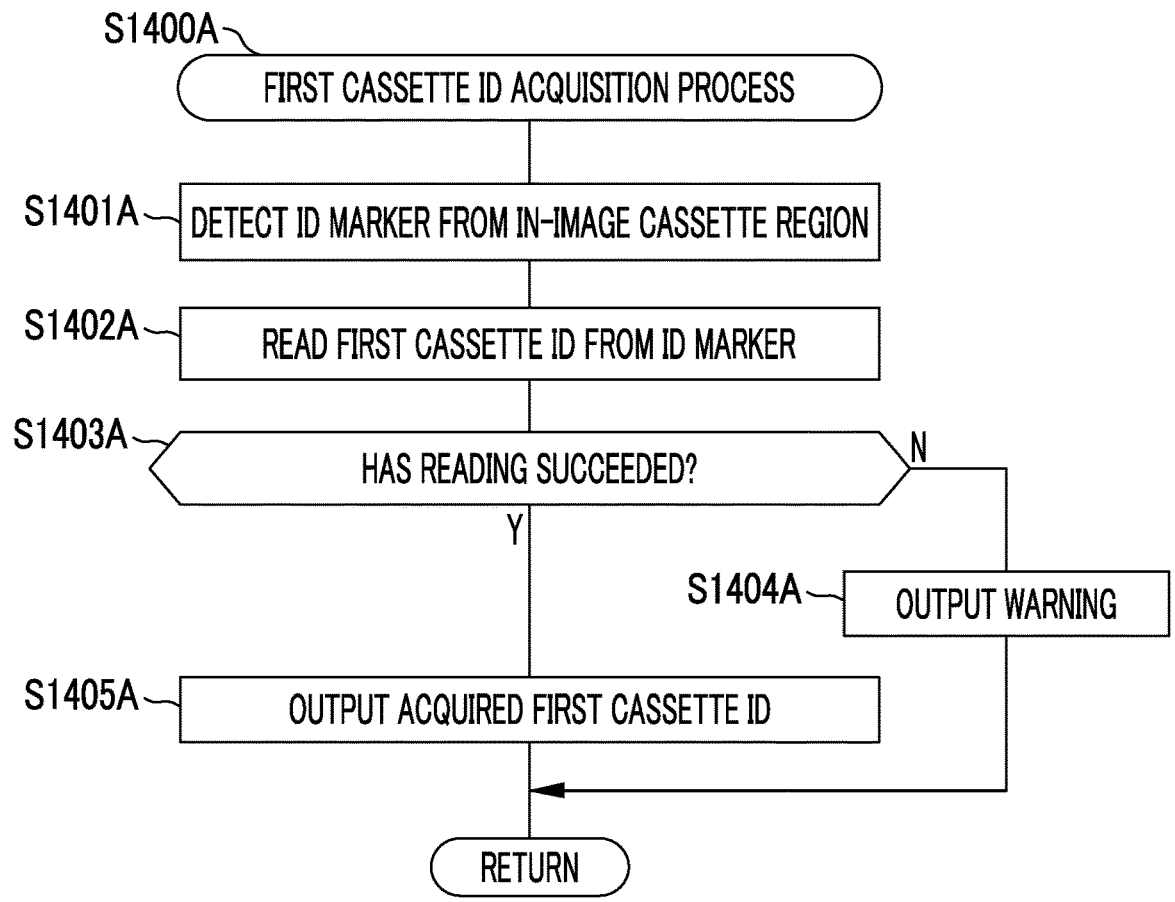
FIG. 19 is a flowchart illustrating the procedure of a first cassette ID acquisition process.

For example, the first cassette ID acquisition process is performed according to the procedure illustrated in the flowchart of S1400A illustrated in FIG. 19. In the first cassette ID acquisition process in S1400A, first, the identification information acquisition unit 73 detects the ID marker 32 from the in-image cassette region 77 in S1401A. Then, in S1402A, the identification information acquisition unit 73 reads the first cassette ID from the ID marker 32.

In a case in which the reading has succeeded in S1403A (Y in S1403A), the identification information acquisition unit 73 outputs the information of the acquired first cassette ID and the in-image cassette region 77 to the use cassette setting unit 74 (S1405A). Then, the process returns the flow illustrated in FIG. 18 and proceeds to S1500. On the other hand, in a case in which the reading has failed in S1403A (N in S1403A), the identification information acquisition unit 73 issues a warning indicating that the ID marker 32 is not readable (S1404A). For example, the warning is performed by displaying a warning message on the touch panel 33 or by outputting a warning sound from the speaker 39. In addition, the warning may be notified to the camera 26 to turn on the indicator 26A, thereby informing the occurrence of an error.

Returning to FIG. 18, in a case in which the first cassette ID has been acquired (Y in S1500), the use cassette setting unit 74 accesses the registered cassette information 57 and acquires the second cassette ID. Then, the first cassette ID and the second cassette ID are collated with each other (S1600). On the other hand, in a case in which the first cassette ID has not been acquired (N in S1500), a warning indicating that the first cassette ID has not been acquired is issued (S1510) and the process proceeds to S2100. In a case in which a camera image acquisition process end command is issued (Y in S2100), the camera image acquisition process ends and the selection operation receiving function ends. In a case in which the end command is not issued, the process returns to S1100.

The use cassette setting unit 74 collates the first cassette ID with the second cassette ID. In a case in which the first cassette ID is matched with any one of the second cassette IDs (Y in S1700), the first cassette ID is detected from the camera image 76 and the electronic cassette 16 with the first cassette ID matched with the second cassette ID is determined to be the registered cassette (S1800).

Figure 20:
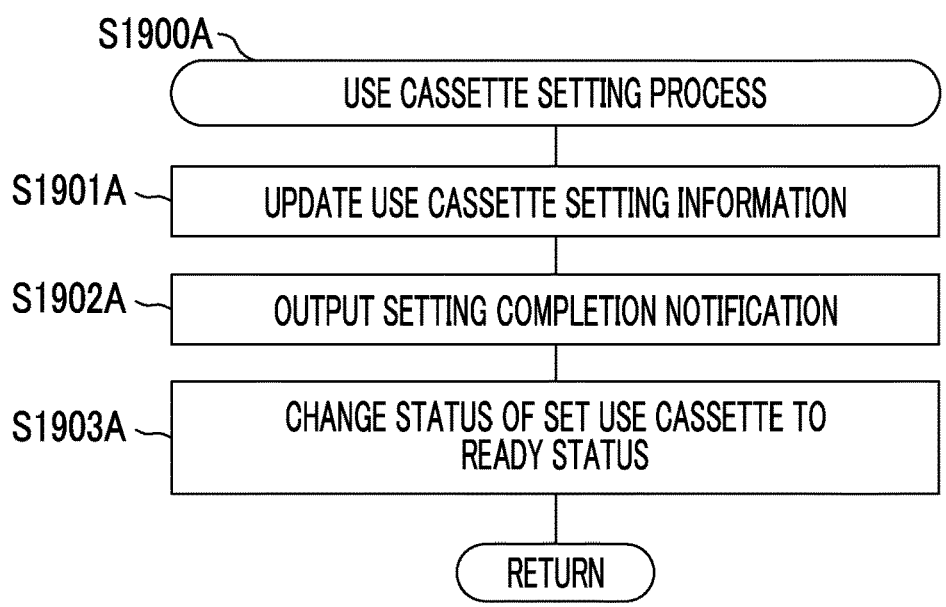
FIG. 20 is a flowchart illustrating the procedure of a use cassette setting process.

In a case in which the electronic cassette 16 is determined to be the registered cassette, the use cassette setting unit 74 performs a use cassette setting process (S1900). As the use cassette setting process in S1900, for example, the use cassette setting process in S1900A illustrated in FIG. 20 is performed. In the process in S1900A, as illustrated in FIG. 12, the use cassette setting information of the electronic cassette 16 (in the example illustrated in FIG. 12, the "cassette C") set as the use cassette is updated.

Then, the use cassette setting unit 74 outputs a setting completion notification (S1902A). The setting completion notification is transmitted to the camera 26 through the network communication unit 54. In a case in which the setting completion notification is received, the camera 26 turns on the indicator 26A to notify the operator OP that the setting has been completed. In addition, the setting completion notification is displayed on the touch panel 33 through the GUI controller 51. The operator OP who stands next to the subject H can check the setting completion notification through the indicator 26A.

Figure 21:
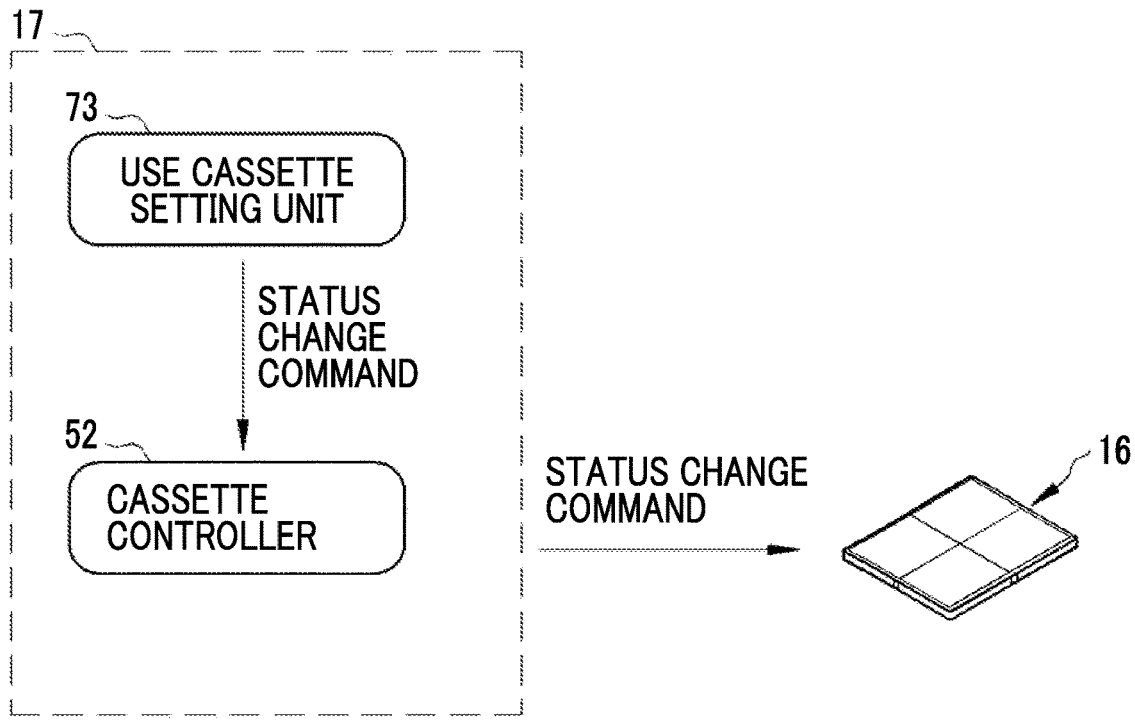
FIG. 21 is a diagram illustrating, a method for transmitting a status change command.

The use cassette setting unit 74 changes the status of the set use cassette to the ready status in which X-ray imaging can be performed (S903A). In many cases, the status of the unset use cassette is in the power saving mode such as the sleep status. In a case in which the status of the use cassette is in the power saving mode, the use cassette setting unit 74 changes to the ready status immediately after the use cassette is set. The change of the status of the set use cassette to the ready status makes it easy to rapidly perform imaging. For example, this process is performed by the transmission of a status change command to the electronic cassette 16 set as the use cassette through the cassette controller 52 by the use cassette setting unit 74 as illustrated in FIG. 21. In this way, preparation for imaging using the electronic cassette 16 set as the use cassette is completed.

In a case in which the first cassette ID is not matched with any of the second cassette IDs in S1700 of FIG. 18 (N in S1700), the use cassette setting unit 74 determines that the detected electronic cassette 16 is not the registered cassette and proceeds to a process in S2000 in a case in which the electronic cassette 16 is not the registered cassette.

For the process in a case in which the electronic cassette 16 is not the registered cassette, for example, the use cassette setting unit 74 issues a warning indicating that the electronic cassette 16 is not the registered cassette as in S2000 illustrated in FIG. 20 (S2001). The warning is performed through the touch panel 33, the speaker 39, and the indicator 26A of the camera 26.

As the warning from the speaker 39, for example, a beep sound for notifying that an error has occurred may be output or a voice message "The electronic cassette 16 has been detected, but is not the registered cassette." may be output. For example, a method is considered which blinks a lamp to notify the occurrence of an error as the warning from the indicator 26A. A message informing the content of the error is displayed on the touch panel 33. In a method that outputs a warning through the touch panel 33, in a case in which the console 17 is not close to the operator OP, the operator OP is not capable of checking the warning. Therefore, a method that outputs a warning through the speaker 39 or the indicator 26A is preferable.

In addition, the use cassette setting unit 74 inquires whether to register the electronic cassette, in addition to the warning (S2002). For example, the inquiry is performed by outputting a voice message "Would you like to register the detected electronic cassette 16 as the registered cassette?" from the speaker 39. As another inquiry process, the same inquiry message may be displayed on the touch panel 33. For this inquiry process, a method through the speaker 39 which makes it unnecessary to check the touch panel 33 is preferable in terms of the convenience of the operator OP.

After performing the inquiry process, the use cassette setting unit 74 waits for a registration command from the operator OP (S2003). As a registration command receiving method, there is a method which receives a registration command input through the operation screen in response to the inquiry message displayed on the touch panel 33 of the console 17.

In addition, as the registration command receiving method, the following method is used. That is, the use cassette setting unit 74 starts a timer after performing the inquiry process in S2002. Then, the use cassette setting unit 74 waits for the lapse of a predetermined time. In a case in which no operations are input from the operator OP after the predetermined time elapsed, the use cassette setting unit 74 regards the registration command as having been issued and receives the registration command.

In addition, the following method may be used: the operator OP issues the registration command by gesture; and the camera 26 detects the gesture to receive the registration command. In this case, the search processing unit 55 needs to include a processing unit that recognizes gesture from the camera image 76. In the method using the timer of the camera 26, even in a case in which the console 17 is not close to the operator OP, it is possible to input the registration command, similarly to the inquiry or the warning. Therefore, the method is preferable.

In a case in which the registration command has been issued, the use cassette setting unit 74 performs a registration process which updates the registered cassette information 57 and registers the detected electronic cassette 16 as the registered cassette (S2004). Then, the process proceeds to S2100 of the flow illustrated in FIG. 18. In a case in which the camera image is continuously acquired, the process of the console 17 returns to S1200. Therefore, the registered electronic cassette 16 is detected from the camera image 76 again. In this case, since the electronic cassette 16 is determined to be the registered cassette in S1800, the electronic cassette 16 is set as the use cassette (S1900).

As such, in the X-ray imaging system 10, the console 17 has the function of receiving the operation of selecting the electronic cassette 16 using the camera 26. Therefore, the operator OP can input the use cassette selection operation only by inserting the electronic cassette 16 desired to be selected as the use cassette into the field of view CV of the camera 26. It is possible to perform the use cassette selection operation, without moving to the place in which the console 17 is provided to directly operate the operation screen of the console 17. Therefore, it is possible to simply pair the electronic cassette 16.

For example, for the imaging room, in some cases, the console 17 is provided in a room, such as a preparation room for imaging, which is different from the imaging room. In this case, it takes a lot of time and effort to move the place in which the console 17 is provided. The invention is particularly effective in this case.

In addition, the invention is effective in a case in which the console 17 is provided close to the operator OP who performs positioning. In many cases, the operator OP who performs positioning holds the electronic cassette 16 in the hands for positioning. The hands are basically required to operate the console 17. Therefore, the operator OP needs to put the electronic cassette 16 held in the hands down, to interrupt positioning, and to operate the console 17. According to the invention, the operator OP can pair the console 17 and the electronic cassette 16 only by performing an operation of inserting the electronic cassette 16 into the field of view CV of the camera 26 while holding the electronic cassette 16 in the hands.

Figure 23:
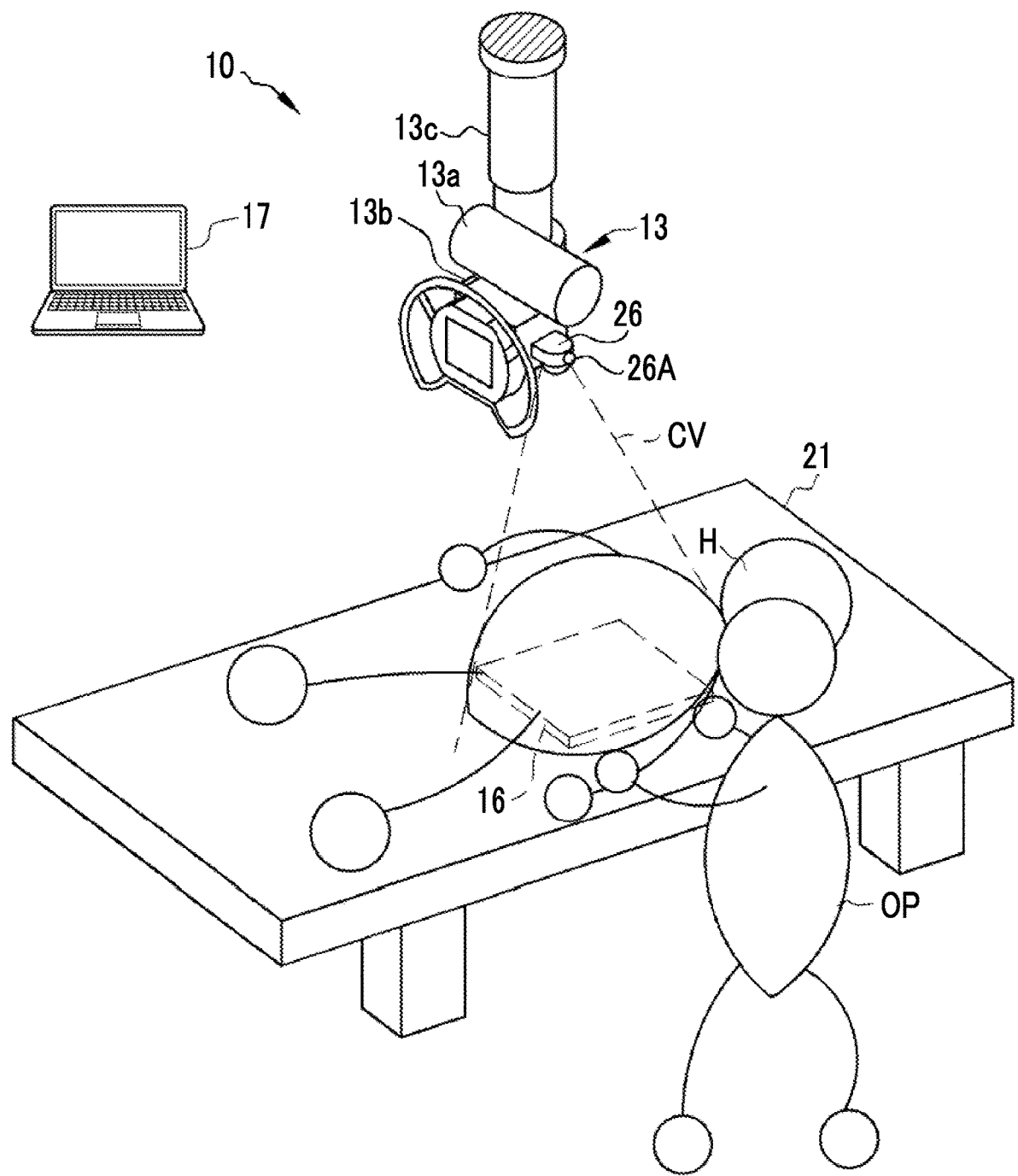
FIG. 23 is a diagram illustrating a state in which positioning has been completed.

After the selection operation is performed, X-ray imaging is performed using the use cassette. As illustrated in FIG. 23, the operator OP completely inserts the electronic cassette 16 between the body and the subject H and the bed 21 and then performs positioning. After the positioning, the operator OP operates the irradiation switch 23. Then, X-rays are emitted from the X-ray generation apparatus 11 to the subject H and an X-ray image of the subject H is acquired by the use cassette. The use cassette transmits the acquired X-ray image to the console 17.

In the flow illustrated in FIG. 18 in this example, the process of acquiring the second cassette ID to be collated with the first cassette ID from the registered cassette information 57 is performed immediately before the collation process in S1600. However, for example, the second cassette ID acquisition process may be performed before the first cassette ID acquisition process in S1400. That is, the second cassette ID acquisition process may be performed at any time before the collation process in S1600.

In this example, the indicator 26A has been described as an element that is attached to the camera 26 provided in the X-ray generation apparatus 11. However, for example, the indicator 26A may not be indirectly provided in the X-ray generation apparatus 11 through the camera 26, but may be directly provided in the X-ray generation apparatus 11. In addition, in a case in which the X-ray generation apparatus 11 includes, for example, a display panel functioning as an operation panel, the display panel may be used as the indicator 26A. In a case in which the indicator 26A is provided in the X-ray generation apparatus 11 in any of the aspects, it is easy for the operator OP who performs positioning to visually recognize the indicator 26A. In addition, the indicator 26A may be a device that is completely independent of the camera 26 or the X-ray generation apparatus 11. In a case in which the indicator 26A is completely independent of the camera 26 or the X-ray generation apparatus 11, the indicator 26A needs to have a communication function for communication with the console 17.

The example in which the camera 26 is provided in the X-ray source 13 has been described. However, the camera 26 may be provided on the ceiling or the wall of the imaging room. In addition, a stand including a support that extends in the vertical direction and an arm whose angle can be adjusted may be provided and the camera 26 may be attached to the leading end of the arm, instead of being provided on the ceiling or the wall. Even in a case in which the camera 26 is provided on the ceiling or the wall, the camera 26 may be attached to the ceiling or the wall through, for example, an arm that can adjust the imaging direction. That is, in a case in which the usage environment of the electronic cassette 16 is a room, the camera 26 may be provided at any position in the room as long as it can view the usage environment. In addition, the camera 26 may be provided in the irradiation opening of the X-ray source 13 and may capture the field of view CV through the irradiation opening.

In this embodiment, a motion picture is given as an example of the camera image 76 output from the camera 26. However, the camera image may be a still image. In the case of the still image, the still images may be captured at a predetermined interval and then sequentially output. In this case, it is possible to check an aspect of a change in the usage environment over time. In addition, the camera image 76 may be used as an image analysis target and may be displayed on the display unit of the touch panel 33 in the console 17.

In a case in which the camera image 76 is displayed on the touch panel 33, the progress of the process performed in the search processing unit 55 may be displayed on the touch panel 33. For example, in a case in which the in-image cassette region 77 is detected as illustrated in FIG. 16, the in-image cassette region 77 may be displayed so as to be visually recognized in the camera image 76. In addition, the display aspect of the in-image cassette region 77 may be represented by a dotted line until the setting of the use cassette is completed and may be represented by a solid line in a case in which the setting of the use cassette has been completed.

In each of the subsequent embodiments including the following second embodiment, the description is focused on a difference from the first embodiment. In addition, the same components as those in the first embodiment are denoted by the same reference numerals and the description thereof will not be repeated.

Second Embodiment

Figure 24:
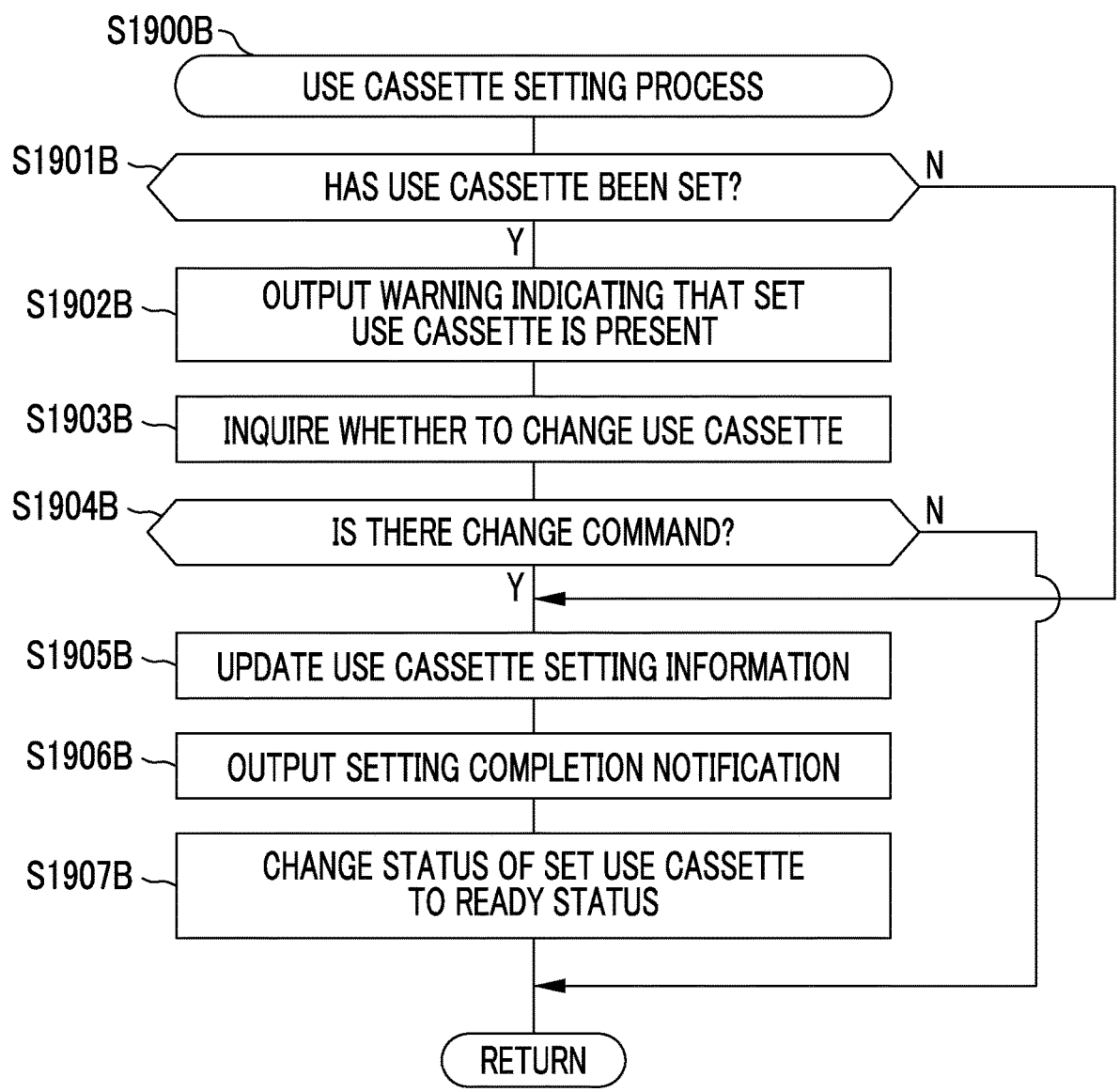
FIG. 24 is a flowchart illustrating the procedure of a use cassette setting process according to a second embodiment.

A second embodiment illustrated in FIGS. 24 and 25 relates to a use cassette setting process in a case in which the use cassette has been set and the registered cassette which is a candidate of the use cassette is newly detected. In the second embodiment, the use cassette setting unit 74 performs a use cassette setting process in S1900B illustrated in FIG. 23 as the use cassette setting process in S1900 in the flow illustrated in FIG. 18.

In FIG. 24, first, the use cassette setting unit 74 checks whether the use cassette has been set with reference to the use cassette setting information 58 (S1901B). In a case in which the use cassette has not been set (N in S1901B), the use cassette setting unit 74 proceeds to S1905B.

In a case in which the use cassette has been set (Y in S1901B), the use cassette setting unit 74 outputs a warning indicating that the use cassette has been set (S1902B). Then, the use cassette setting unit 74 performs a process of inquiring whether to change the set use cassette to a newly detected registered cassette (S1903B). The use cassette setting unit 74 waits for the input of a change command from the operator OP (S1904B). In a case in which the change command is received (Y in S1904B), the use cassette setting unit 74 proceeds to S1905B.

Figure 22:
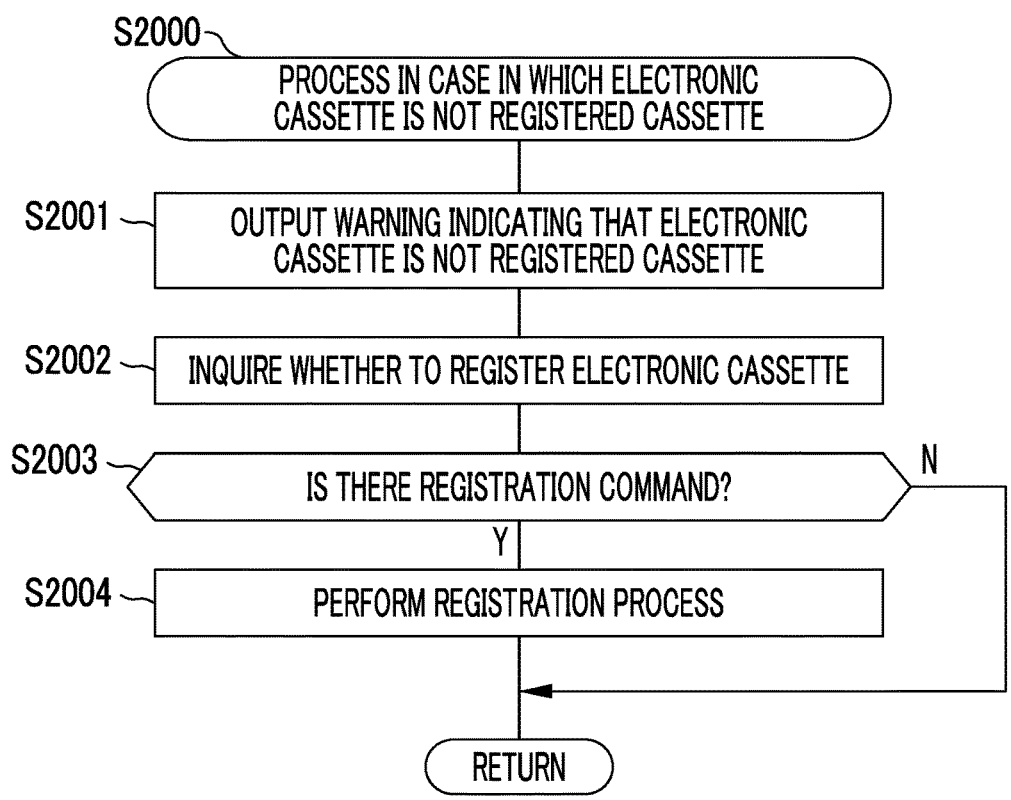
FIG. 22 is a flowchart illustrating the procedure of a process in a case in which the detected electronic cassette is not the registered cassette.

The warning, the inquiry, and the reception of the change command are performed by the same processes as those in S2002 to S2004 illustrated in FIG. 22. That is, the warning, the inquiry, and the reception of the change command are performed using at least one of the touch panel 33, the speaker 39, or the indicator 26A. For a method for receiving the change command, similarly to the reception of the registration command in S2003 of FIG. 22, a method may be used which regards the change command as having been input in a case in which a predetermined time has elapsed since the inquiry. With this configuration, the operator OP can input the change command to the console 17, without interrupting positioning. In addition, as described in the aspect of the reception of the registration command in S2003 of FIG. 22, the camera 26 may be used to receive the change command that is input by gesture from the operator OP.

In a case in which the change command is received (Y in S1904B), the use cassette setting unit 74 updates the use cassette setting information (S1905B). The update of the use cassette setting information in S1905B is performed as illustrated in FIG. 25. FIG. 25 illustrates an example in which the use cassette is changed from the cassette C to the cassette A in a case in which the use cassette has been set to the cassette C. The setting information item or the imaging order item is updated. In this way, the use cassette paired with the console 17 is changed.

In a case in which the use cassette setting information is updated, a setting completion notification is output (S1906B) and the status of the set use cassette is changed to the ready status (S1907B). A process in S1906B and S1907B is the same as the process in S1902A and S1903A illustrated in FIG. 20. In a case in which the status is changed, the use cassette setting information 58 is also updated.

In the actual imaging spot, as such, the paired use cassette is frequently changed to another electronic cassette. For example, during positioning, the operator sees the body type of a patient, feels that the size of the paired use cassette is small, and changes the use cassette to another electronic cassette with a large size. In a case in which the remaining battery level of the use cassette is low immediately before imaging, the operator changes the use cassette to another electronic cassette with a high remaining battery level. In this example, even in these cases, it is possible to change the use cassette, without interrupting positioning for operating the console 17. Therefore, this configuration is very convenient.

Third Embodiment

Figure 26:
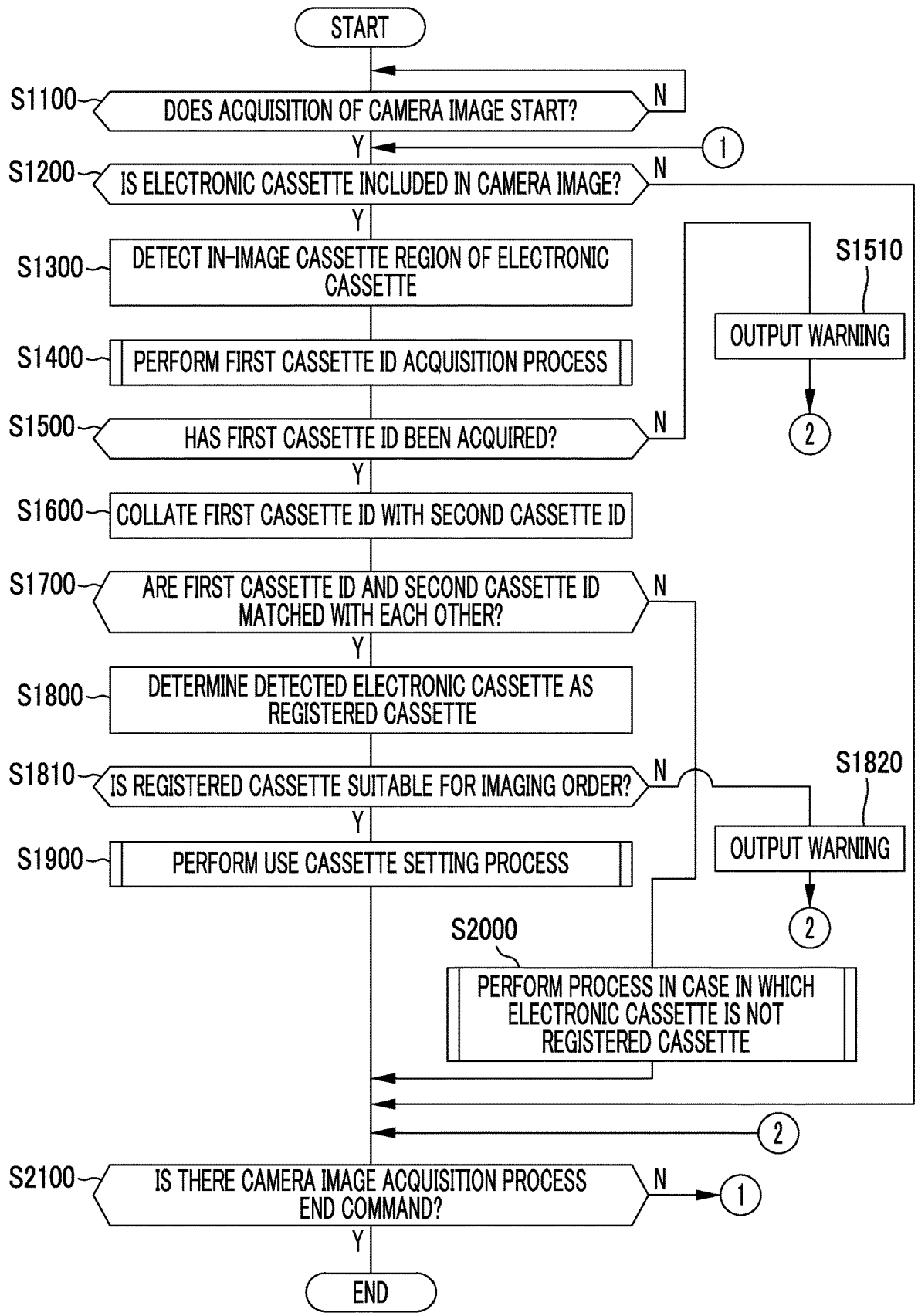
FIG. 26 is a flowchart illustrating the procedure of a selection operation receiving process according to a third embodiment.

In a third embodiment illustrated in FIG. 26, the use cassette setting unit 74 determines suitability for an imaging order and sets a registered cassette suitable for the imaging order as the use cassette, in addition to the process of determining whether the electronic cassette 16 detected in the camera image 76 is the registered cassette.

A flowchart illustrated in FIG. 26 is the same as that illustrated in FIG. 18 except that a process in S1810 and S1820 is added. In a case in which the detected electronic cassette 16 is determined to be the registered cassette, the use cassette setting unit 74 collates the content of the imaging order with the specification information registered for the registered cassette to determine the suitability of the registered cassette.

As illustrated in FIG. 8, the imaging order is registered in the imaging order information 59. The use cassette setting unit 74 functions as an imaging order acquisition unit that acquires the imaging order from the imaging order information 59. The imaging order includes information of an imaging part or an imaging procedure. Specification information including the plane size of each registered cassette is registered in the registered cassette information 57 in advance. The use cassette setting unit 74 collates the content of the imaging order with the specification information to determine the suitability of the registered cassette for the imaging order.

Then, in a case in which the registered cassette is suitable (Y in S1810), the use cassette setting unit 74 proceeds to S1900 and sets the registered cassette as the use cassette. On the other hand, in a case in which the registered cassette is not suitable, the use cassette setting unit 74 outputs a warning indicating that the registered cassette is not suitable (S1820). The warning is performed by a method using at least one of the touch panel 33, the speaker 39, or the indicator 26A.

As such, since suitability for the imaging order is determined, it is possible to prevent the electronic cassette 16 that is not suitable for imaging from being set as the use cassette. Therefore, it is possible to prevent a situation in which an inappropriate electronic cassette 16 is used for X-ray imaging and X-ray imaging needs to be performed again.

Fourth Embodiment

In a fourth embodiment illustrated in FIGS. 27 to 30, the identification information acquisition unit 73 detects identification light emitted from an indicator 84 that is provided in the electronic cassette 16 and acquires the first cassette ID from the camera image 76. In the first embodiment, for the first cassette ID acquisition process in S1400 of FIG. 18, the first cassette ID is acquired from the ID marker 32 as illustrated in S1400A of FIG. 19. Instead of acquiring the first cassette ID from the ID marker 32 as in the first embodiment, the identification information acquisition unit 73 may acquire the first cassette ID from the identification light emitted from the indicator 84 as in the fourth embodiment.

Figure 27:
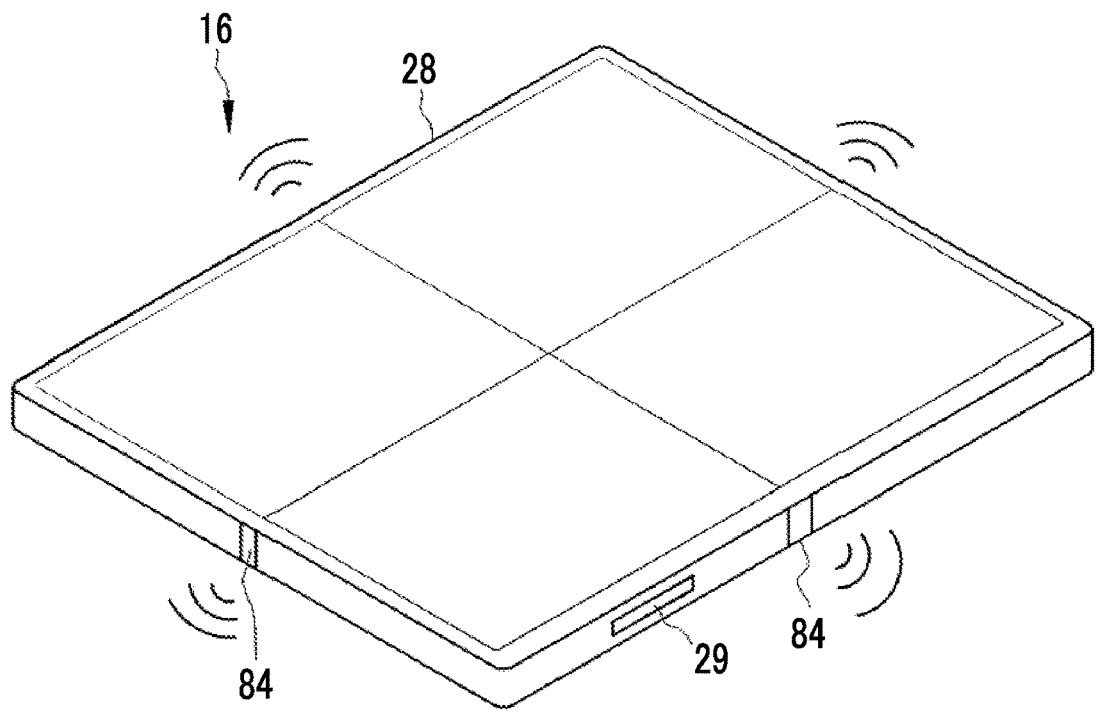
FIG. 27 is a perspective view illustrating a front surface side of an electronic cassette according to a fourth embodiment.
Figure 28:
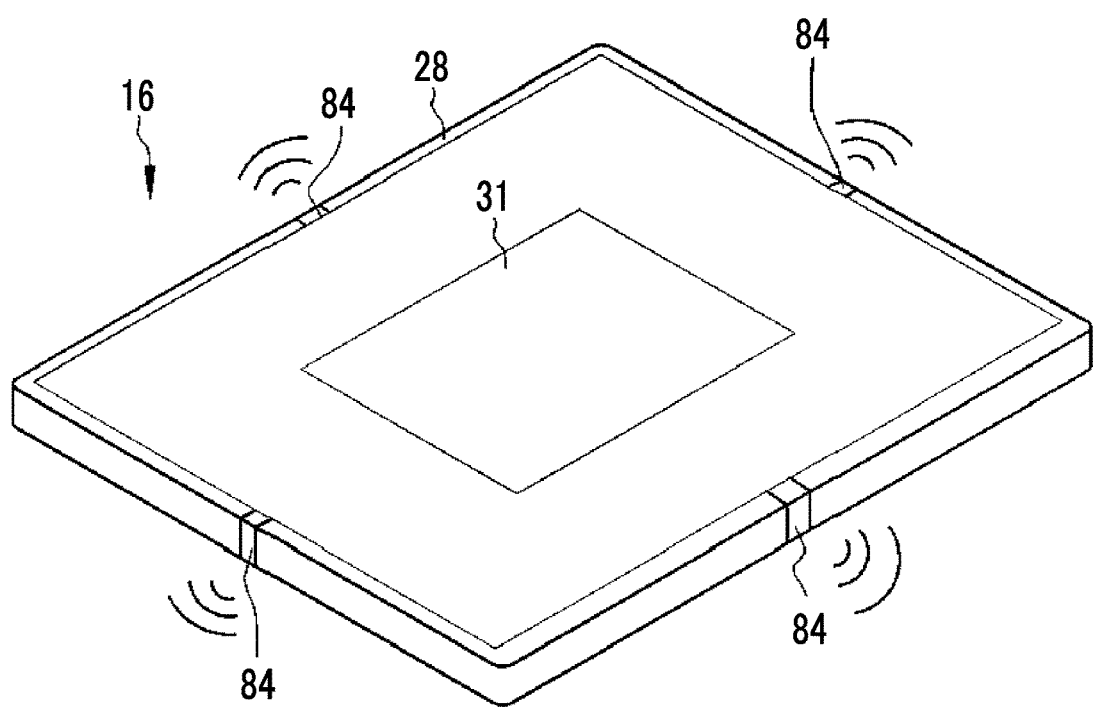
FIG. 28 is a perspective view illustrating a rear surface side of the electronic cassette according to the fourth embodiment.

As illustrated in FIGS. 27 and 28, in the fourth embodiment, for example, the indicator 84 is provided at the center of each of four side surfaces of the housing 28 of the electronic cassette 16. The indicator 84 is a light source such as a light emitting diode (LED). The indicator 84 can emit identification light of a plurality of colors such as red, blue, and green.

Figure 29:
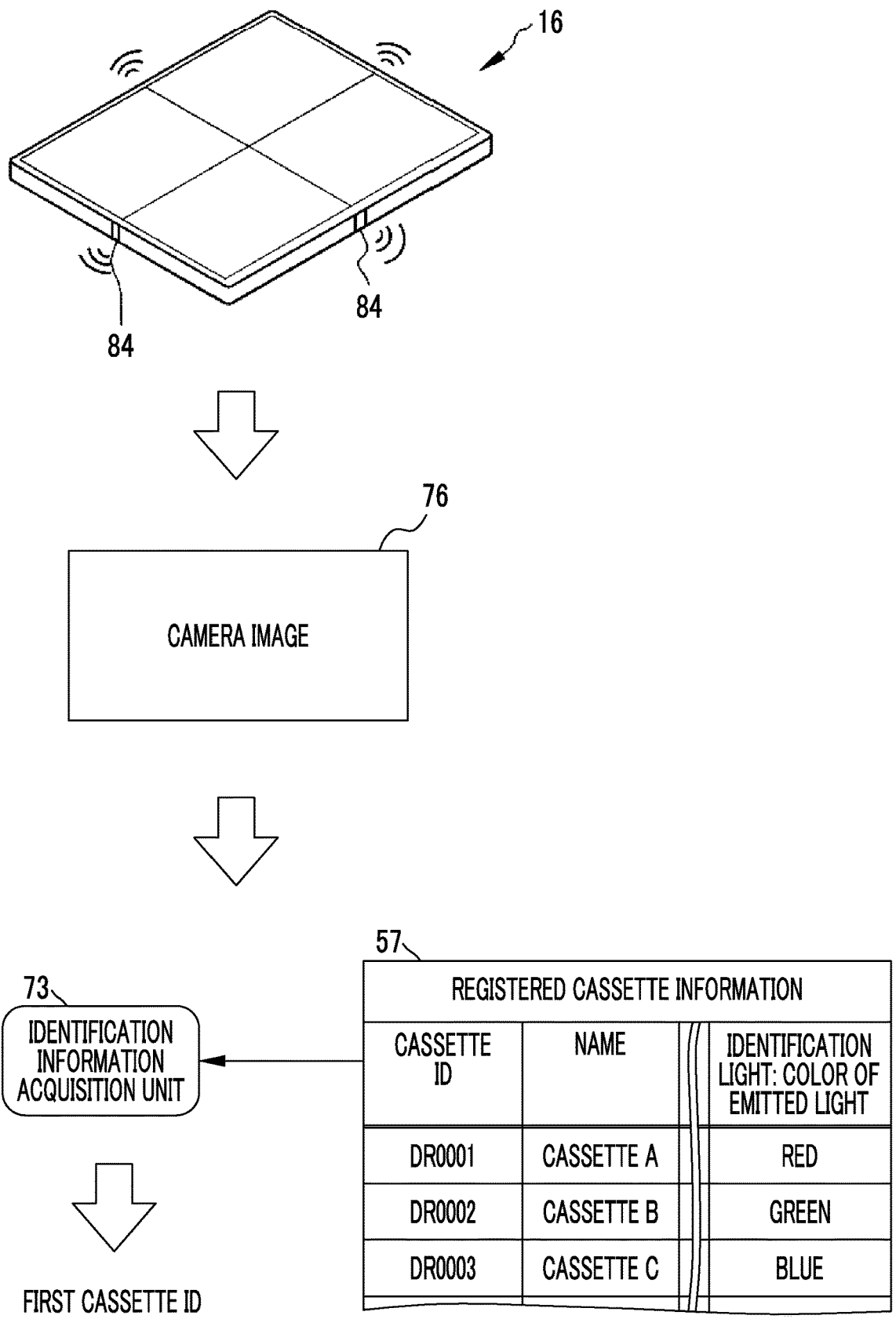
FIG. 29 is a diagram illustrating the outline of a process according to the fourth embodiment.

In the fourth embodiment, as illustrated in FIG. 29, in the registered cassette information 57 of the console 17, the color of the identification light is allocated to each registered electronic cassette 16. In this example, "red" is allocated to an electronic cassette 16A with a cassette ID "DR0001", "green" is allocated to an electronic cassette 16B with a cassette ID "DR0002", and "blue" is allocated to an electronic cassette 16C with a cassette ID "DR0003". The identification information acquisition unit 73 reads the cassette ID from the identification light with reference to the registered cassette information 57.

Figure 30:
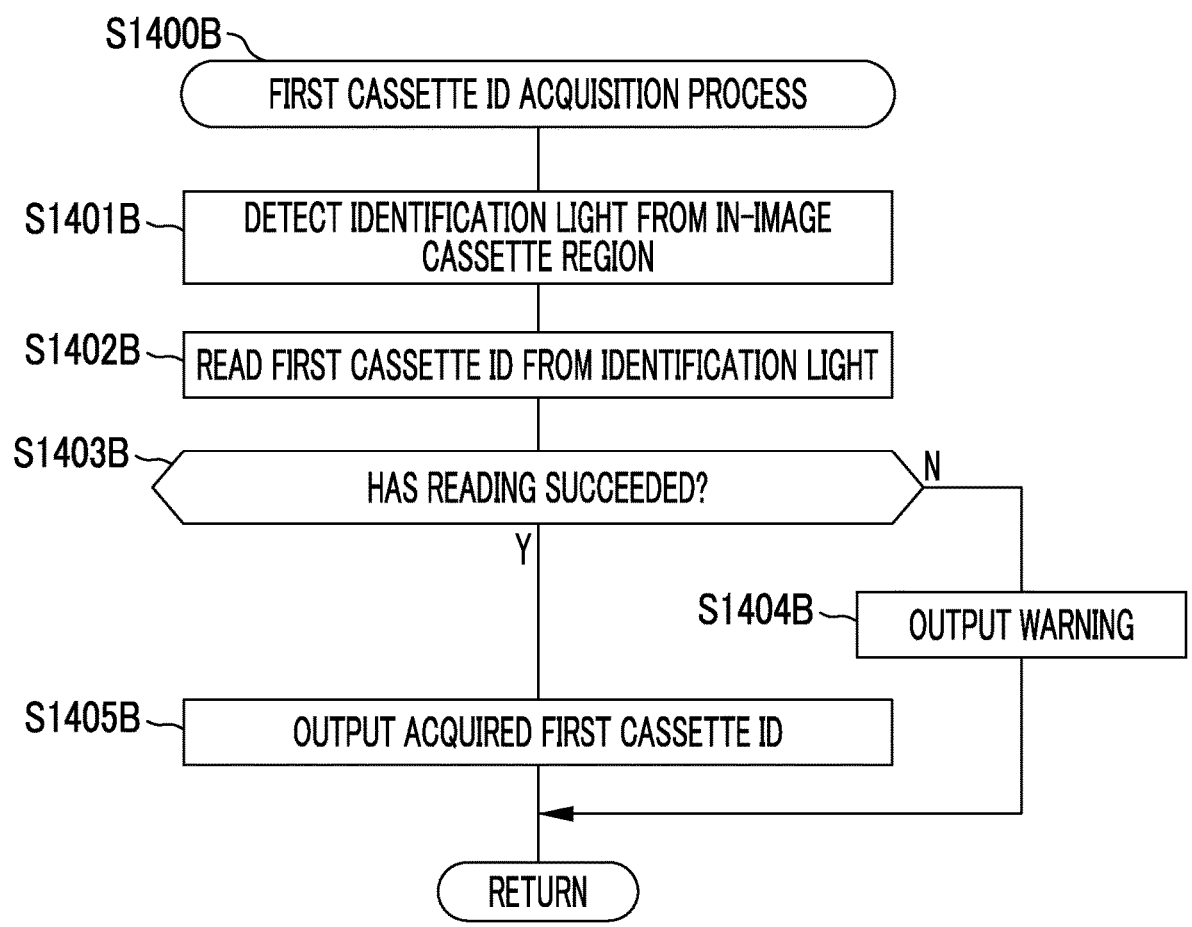
FIG. 30 is a flowchart illustrating the procedure of a first cassette ID acquisition process according to the fourth embodiment.

In the fourth embodiment, the identification information acquisition unit 73 performs the first cassette ID acquisition process in S1400B of FIG. 30 as the first cassette ID acquisition process in S1400 of FIG. 18, instead of the process in S1400A of FIG. 19 in the first embodiment. The identification information acquisition unit 73 detects the identification light emitted from the indicator 84 from the in-image cassette region 77 detected by the in-image cassette detection unit 72 (S1401B). Then, the identification information acquisition unit 73 identifies the color of the identification light and reads the first cassette ID with reference to the correspondence relationship between the identification light and the cassette ID of the registered cassette information 57 (S1402B). In a case in which the reading of the first cassette ID has failed (N in S1403B), the identification information acquisition unit 73 outputs a warning (S1404B). The subsequent process in S1405B is the same as the process in S1405A described in FIG. 19.

In this example, the identification light is identified on the basis of the color and the cassette ID is read. However, the identification light may be identified on the basis of a lighting pattern or a lighting time, instead of the color. The lighting pattern is identified by, for example, a flashing cycle. The lighting time is, for example, the time until the indicator 84 is turned on after a lighting command is transmitted from the console 17 to the electronic cassette 16. The lighting pattern or the lighting time is recorded for each cassette ID in the registered cassette information 57 in advance. In this case, the identification information acquisition unit 73 reads the first cassette ID with reference to the registered cassette information 57 using the method illustrated in FIGS. 29 and 30.

According to the fourth embodiment, it is possible to acquire the cassette ID, without providing the ID marker 32 in the housing 28.

Fifth Embodiment

Figure 31:
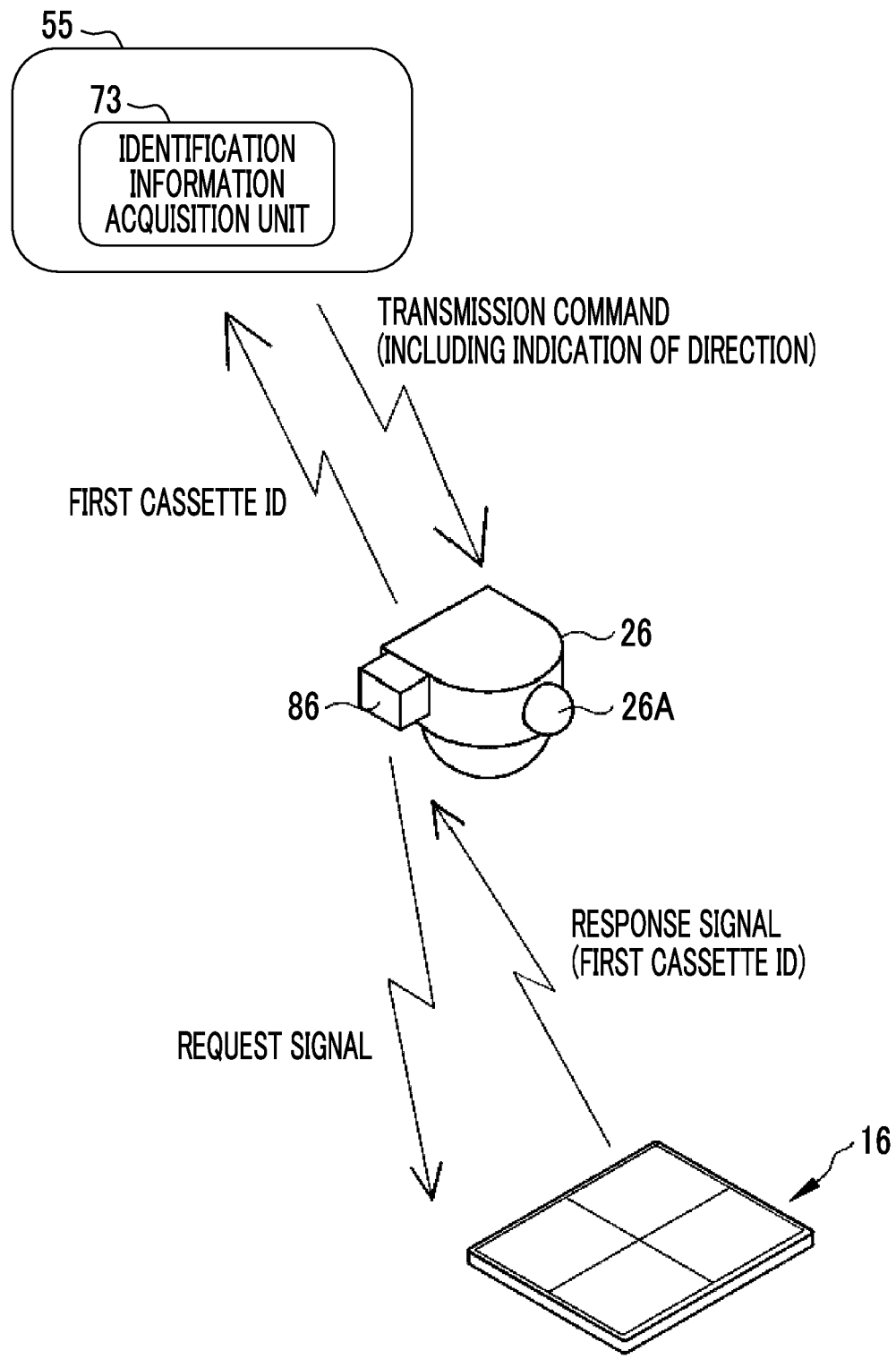
FIG. 31 is a diagram illustrating the outline of a process according to a fifth embodiment.

In a fifth embodiment illustrated in FIGS. 31 and 32, an identification information request signal (hereinafter, simply referred to as a request signal) that requests the first cassette ID is transmitted to the electronic cassette 16 and the first cassette ID is acquired as a response from the electronic cassette 16.

In the fifth embodiment, a request signal transmission unit 86 that transmits the request signal is provided in the vicinity of the camera 26 (for example, on the outer surface of the camera 26). The request signal transmission unit 86 transmits the request signal to the electronic cassette 16 in the usage environment and receives a response signal from the electronic cassette 16 that has received the request signal. In addition, the request signal transmission unit 86 is connected to the network 43, similarly to the camera 26, and can communicate with the console 17.

The request signal is, for example, light, electromagnetic waves, or sound waves with directionality. The request signal transmission unit 86 has a direction control function of transmitting the request signal in a direction in which the electronic cassette 16 is present. The direction control function is implemented by, for example, a method which provides a rotation mechanism for rotating a transmitter that transmits the request signal in the request signal transmission unit 86 or a method which provides a plurality of transmitters in different directions in the request signal transmission unit 86. In this case, the electronic cassette 16 is provided with a transmitting and receiving unit that receives the request signal and transmits a response signal according to the form of the request signal such as light, electromagnetic waves, or sound waves.

Even in a case in which other electronic cassettes 16 are present in the usage environment, the request signal that has been transmitted to a specific electronic cassette 16 by the direction control function of the request signal transmission unit 86 is not received by other electronic cassettes 16. Therefore, a response signal to the request signal can be determined to be a response signal transmitted from the electronic cassette 16 that is present in the transmission direction of the request signal.

The identification information acquisition unit 73 functions as a direction detection unit that detects the direction in which the electronic cassette 16 is present in the usage environment on the basis of the in-image cassette region 77 input from the in-image cassette detection unit 72. Since the request signal transmission unit 86 is provided in the vicinity of the camera 26, the direction of the electronic cassette 16 detected by the identification information acquisition unit 73 on the basis of the camera image 76 is substantially matched with the actual direction in which the electronic cassette 16 is present in the usage environment.

The search processing unit 55 transmits a transmission command including the indication of the direction detected by the identification information acquisition unit 73 to the request signal transmission unit 86 through the network 43. The request signal transmission unit 86 transmits the request signal in the indicated direction, that is, the direction detected by the identification information acquisition unit 73 (direction detection unit) in response to the received transmission command and receives a response signal. The request signal transmission unit 86 transmits the response signal to the console 17 through the network 43.

Figure 32:
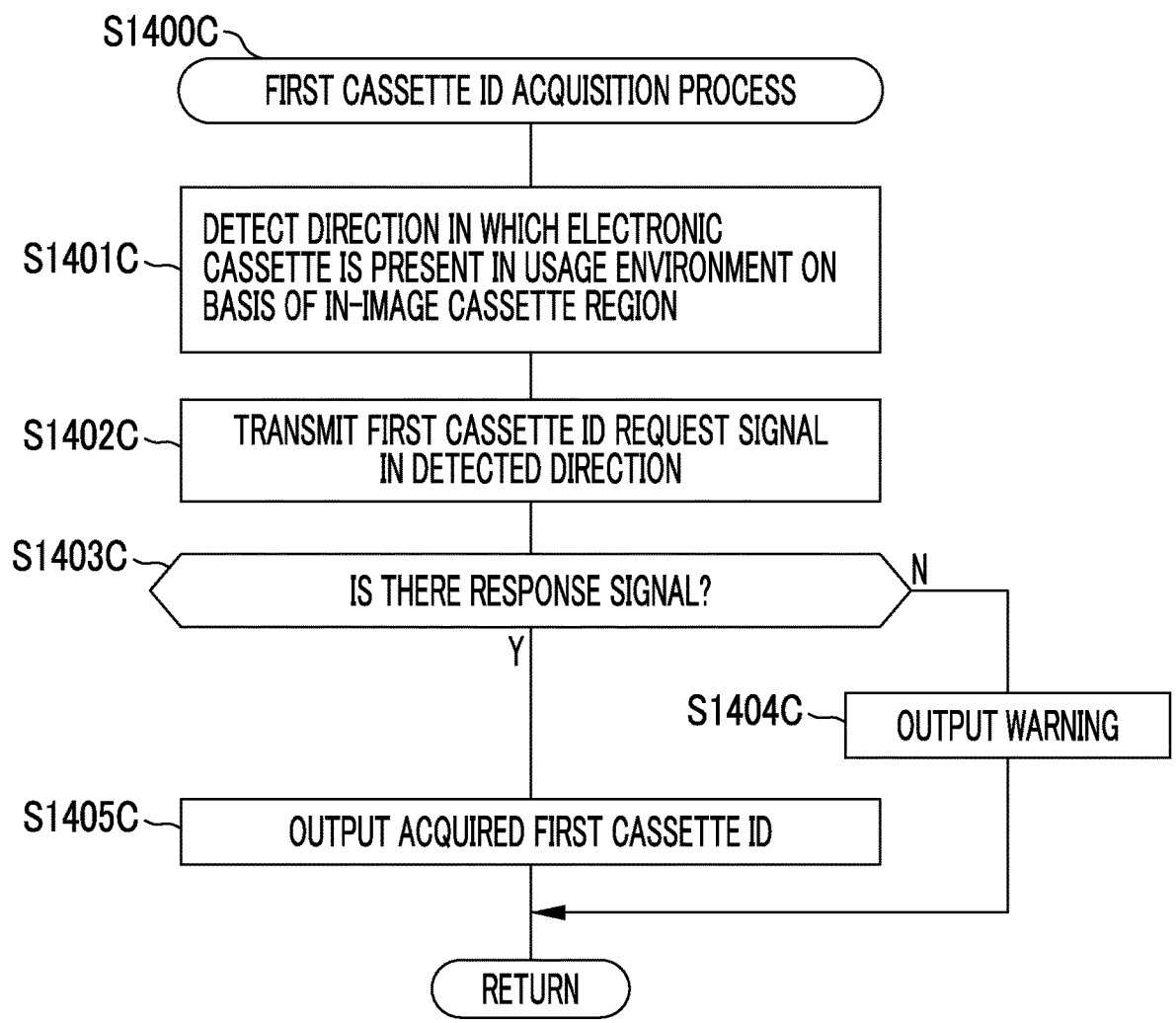
FIG. 32 is a flowchart illustrating the procedure of a first cassette ID acquisition process according to the fifth embodiment.

In the fifth embodiment, for the first cassette ID acquisition process in S1400 illustrated in FIG. 18, a first cassette ID acquisition process in S1400C illustrated in FIG. 32 is performed. The identification information acquisition unit 73 detects the direction in which the electronic cassette 16 is present in the usage environment on the basis of the in-image cassette region 77 detected by the in-image cassette detection unit 72 (S1401C).

The request signal transmission unit 86 transmits a first cassette ID request signal in the detected direction (S1402C). In a case in which the request signal transmission unit 86 receives a response signal (Y in S1403C), a response signal including the first cassette ID is transmitted to the console 17. Then, the identification information acquisition unit 73 acquires the first cassette ID. In a case in which the request signal transmission unit 86 does not receive a response signal (N in S1403C), a warning indicating that a response signal (first cassette ID) is not capable of being received is issued (S1404C). The subsequent process in S1405C is the same as that in S1405A described in FIG. 19.

Modification Example

Figure 33:
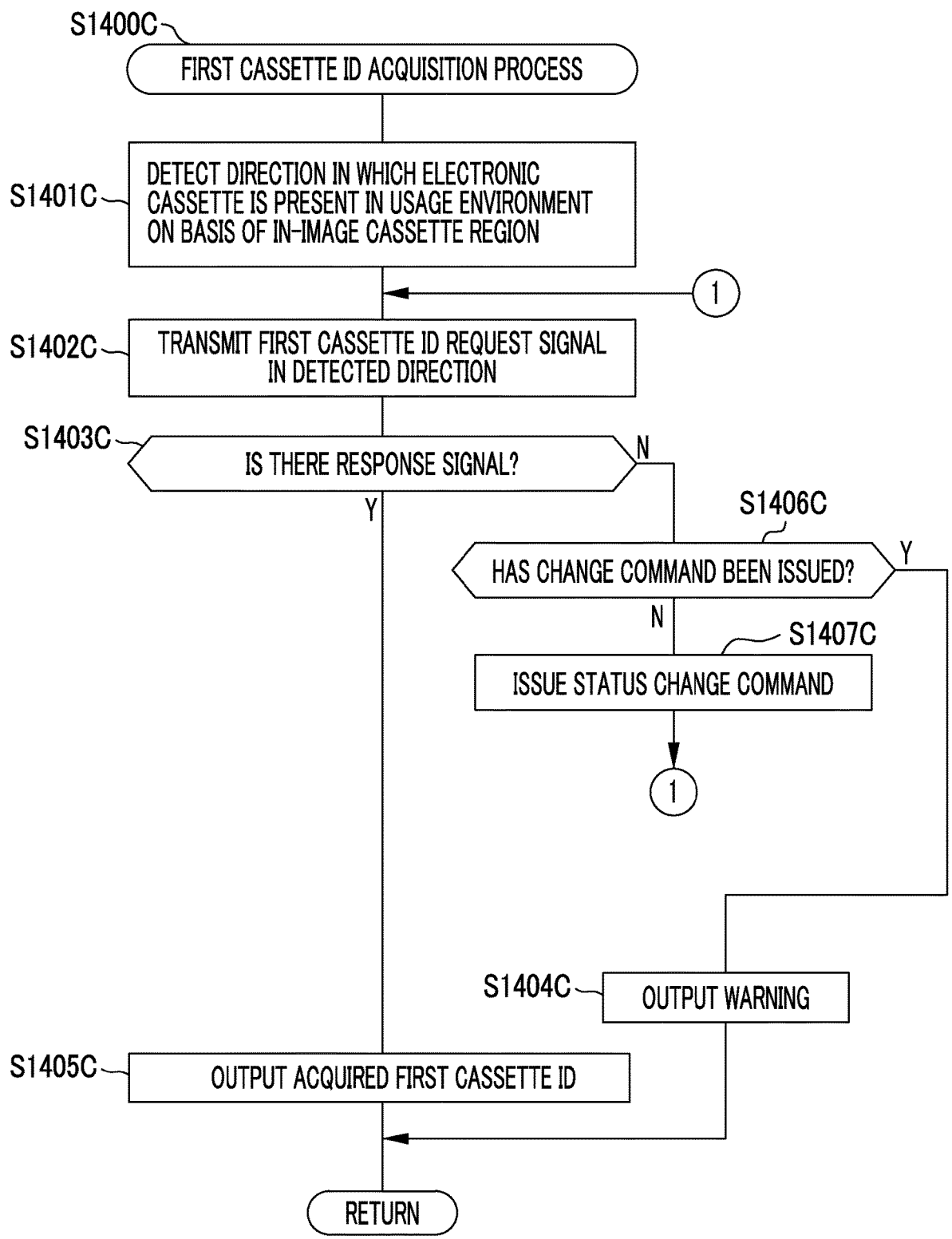
FIG. 33 is a flowchart illustrating a modification example of the fifth embodiment.

A process in a case in which there are no response signals in S1403C of FIG. 32 (N in S1403C) may be performed as illustrated in FIG. 33. The flow illustrated in FIG. 33 is an example on the assumption that the response signal is not capable of being received since the electronic cassette 16 is in a status in which the electronic cassette 16 is not capable of responding to the request signal. In a case in which there is no response, the identification information acquisition unit 73 transmits, to the electronic cassette 16, a status change command to change the status of the electronic cassette 16 to a status in which the electronic cassette can respond to the request signal.

First, in a case in which a response signal is not capable of being received (S1403C), the identification information acquisition unit 73 checks whether the status change command has been issued (S1406C). In a case in which the status change command has been issued, it is considered that the response signal is not capable of being received for a reason which is not related to the status of the electronic cassette 16. In this case, it is meaningless to transmit the status change command again.

In a case in which the status change command has not been issued (N in S1406C), the identification information acquisition unit 73 issues the status change command through the cassette controller 52 (S1407C). Then, the identification information acquisition unit 73 returns to S1403 and transmits the request signal again. On the other hand, in a case in which the status change command has been issued (Y in S1406), the identification information acquisition unit 73 outputs a warning indicating that the response signal is not capable of being received (S1404C). The other processes are the same as those in FIG. 32.

Sixth Embodiment

Figure 35:
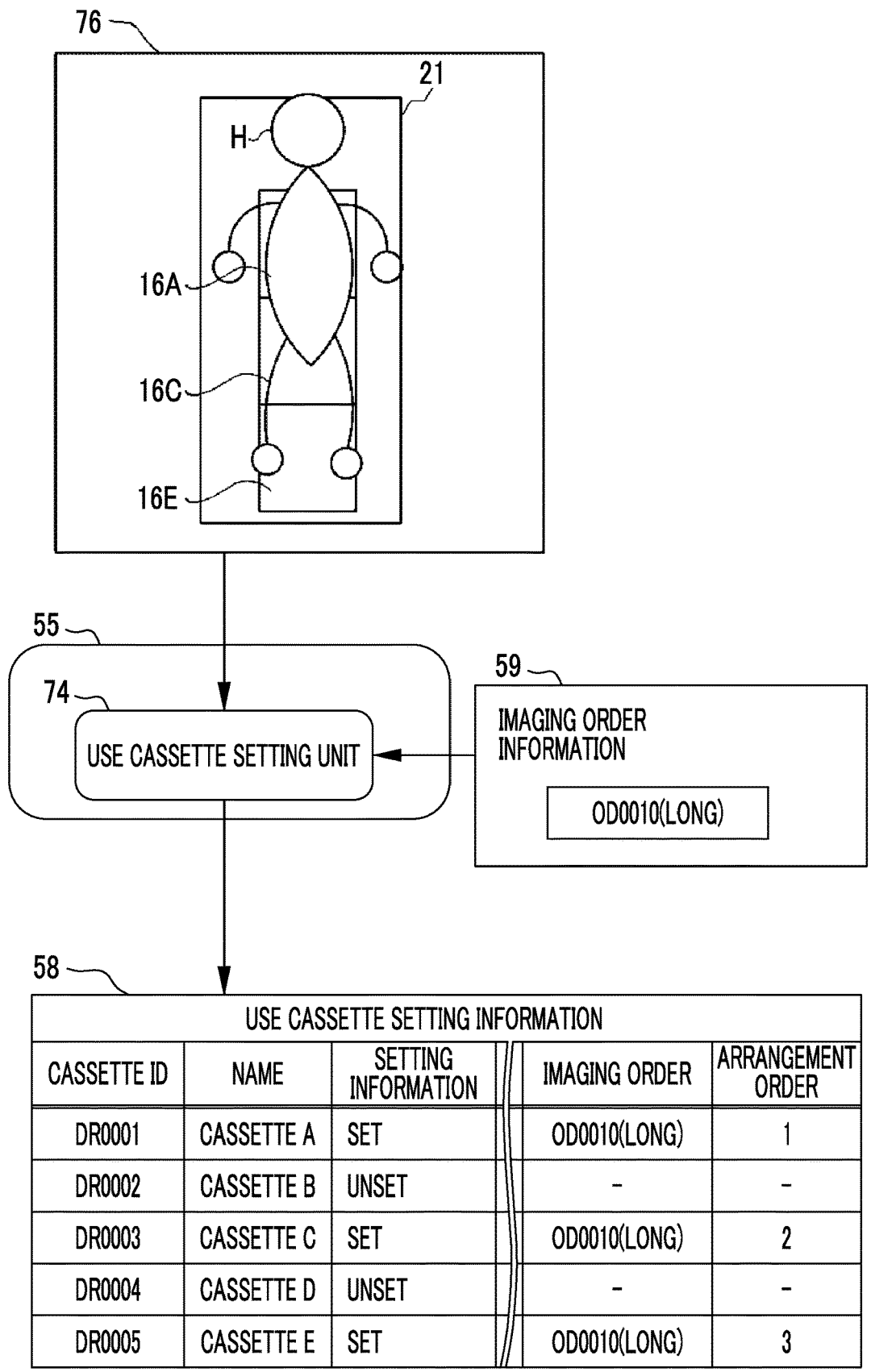
FIG. 35 is a diagram illustrating the outline of a process according to the sixth embodiment.

In a sixth embodiment illustrated in FIGS. 34 and 35, the function of receiving the operation of selecting the electronic cassette 16 is applied to a case in which long-length imaging is performed using the plurality of electronic cassettes 16.

As illustrated in FIG. 34, in the long-length imaging, for example, two or more electronic cassettes 16 are arranged in order to capture an image of a long range such as the whole lower limb of the subject H. The plurality of electronic cassettes 16 are irradiated with X-rays sequentially or at the same time. Then, a plurality of X-ray images detected by each electronic cassette 16 are combined to generate one X-ray image indicating a long imaging range such as the whole lower limb of the subject H.

In the long-length imaging, in a case in which three electronic cassettes 16A, 16C, and 16E are used as illustrated in (A) of FIG. 34, the electronic cassettes 16A, 16C, and 16E are arranged in a line on the bed 21 on which the subject H lies. As illustrated in (B) of FIG. 34, the search processing unit 55 captures this aspect with the camera 26 to obtain a camera image 76.

As illustrated in FIG. 35, the search processing unit 55 detects a plurality of electronic cassettes 16 from the camera image 76. The use cassette setting unit 74 determines whether the plurality of electronic cassettes 16 included in the camera image 76 are the registered cassettes. In a case in which the plurality of electronic cassettes 16 are the registered cassettes, the use cassette setting unit 74 reads the content of an imaging order from the imaging order information 59 and determines the suitability of each electronic cassette 16 for the imaging order.

For the suitability for the imaging order, the number of electronic cassettes 16 designated by the imaging order is determined. For example, in a case in which three electronic cassettes 16 are designated by an imaging order in long-length imaging, the use cassette setting unit 74 determines whether the designated number of electronic cassettes 16 is included in the camera image 76. In a case in which the designated number of electronic cassettes 16 is not included in the camera image 76, the use cassette setting unit 74 outputs a warning indicating that the designated number of electronic cassettes 16 is not included in the camera image 76.

In addition, for the suitability for the imaging order, the determination of the suitability for the imaging order performed in the third embodiment illustrated in FIG. 26 may be performed for each electronic cassette 16.

In a case in which the electronic cassette 16 is suitable for the imaging order, as illustrated in FIG. 35, the use cassette setting unit 74 updates the use cassette setting information 58 and sets the plurality of detected electronic cassettes 16 as the use cassettes.

Seventh Embodiment

Figure 36:
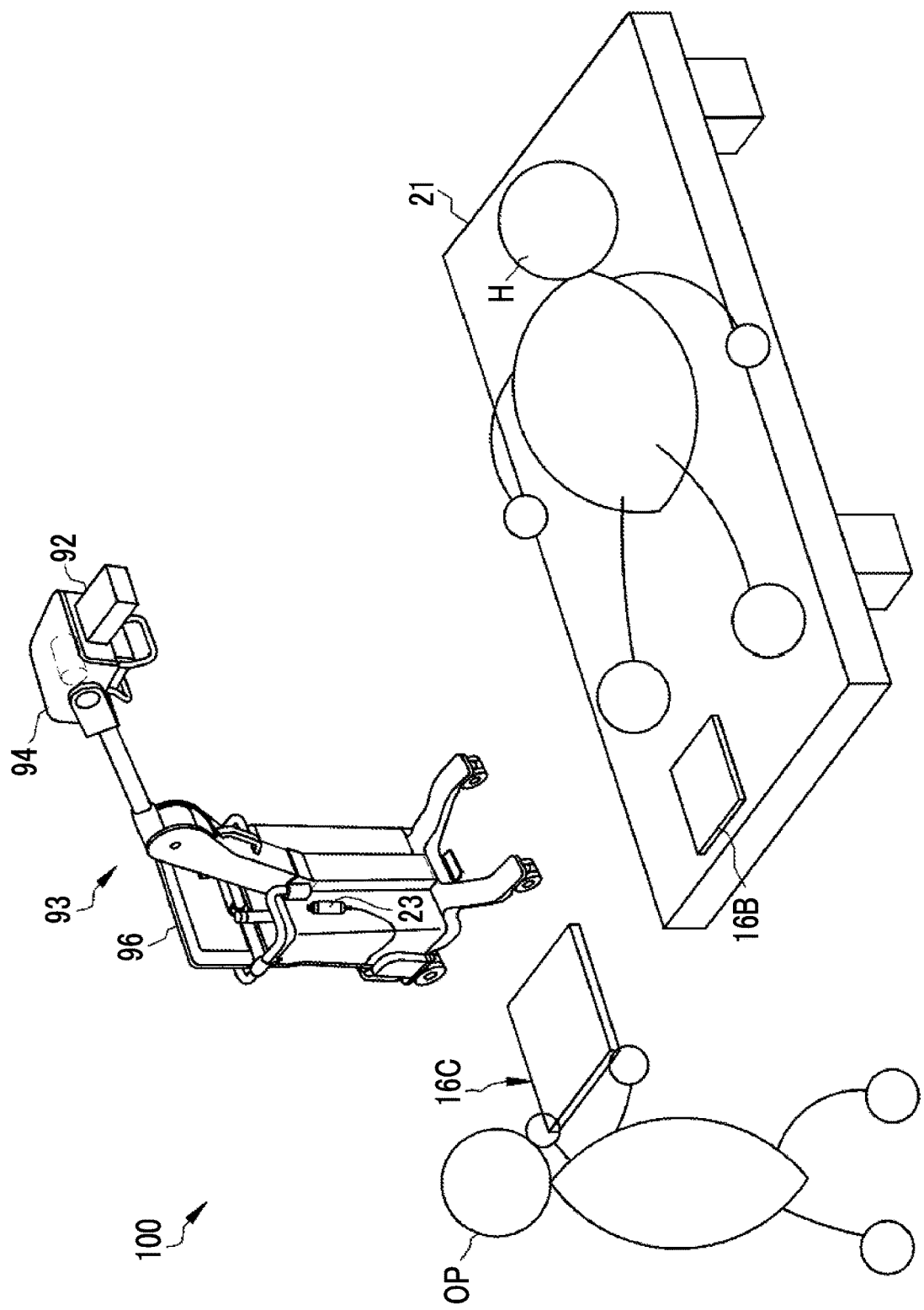
FIG. 36 is a diagram illustrating an example in which a camera is provided in a treatment cart in a seventh embodiment.

A seventh embodiment illustrated in FIG. 36 relates to an example in which the camera 92 is not provided in the X-ray source 13 hung from the ceiling of the imaging room, but is provided in a treatment cart 93. The treatment cart 93 has, for example, the functions of an X-ray generation apparatus including an X-ray source 94 and the functions of a console on a carriage that can travel. The treatment cart 93 is provided with a touch panel 96 as a display unit of the console. An X-ray imaging system 100 includes the treatment cart 93 and the electronic cassette 16.

A camera 92 has the same functions as the camera 26 and is provided on a housing of the X-ray source 94. The camera 92 outputs the camera image 76 similarly to the camera 26 and the camera image 76 is displayed on the touch panel 96. As such, in a case in which the camera 92 is provided in the treatment cart 93, it is also possible to capture the environment in which the electronic cassette 16 is used. Therefore, the use of the X-ray imaging system 100 makes it possible to achieve the same function of receiving the electronic cassette selection operation as that in each of the above-described embodiments.

In each of the above-described embodiments, the example in which the console 17 has the function of receiving the electronic cassette selection operation has been described. However, the selection operation receiving function may be provided in an apparatus other than the console 17 or may be provided in a dedicated apparatus.

The camera image 76 according to each of the above-described embodiments may be used to check the external injuries of a patient, in addition to being used for the function of receiving the electronic cassette selection operation.

In each of the above-described embodiments, for example, the hardware structures of the processing units performing various processes, such as the GUI controller 51, the search processing unit 55, the in-image cassette detection unit 72, the identification information acquisition unit 73, and the use cassette setting unit 74, are the following various processors.

Various processors include, for example, a CPU, a programmable logic device (PLD), and a dedicated electric circuit. The CPU is a general-purpose processor that executes software (program) to function as various processing units as it is known. The PLD is a processor whose circuit configuration can be changed after it is manufactured, such as a field programmable gate array (FPGA). The dedicated electric circuit is a processor having a dedicated circuit configuration designed to perform a specific process, such as an application specific integrated circuit (ASIC).

One processing unit may be one of the various processors or a combination of two or more processors of the same type or different types (for example, a combination of a plurality of FPGAs and a combination of a CPU and an FPGA). In addition, a plurality of processing units may be formed by one processor. As an example in which a plurality of processing units are formed by one processor, first, one processor is formed by a combination of one or more CPUs and software and the processor functions as the plurality of processing units. Second, a processor which is typified by a system-on-chip (SoC) and in which the overall function of a system including a plurality of processing units is implemented by one IC chip is used. As such, the hardware structure of various processing units is formed by one or more of the various processors.

In addition, specifically, the hardware structure of the various processors is an electric circuit (circuitry) which is a combination of circuit elements such as semiconductor elements.

An invention described in the following Supplementary Note 1 can be understood from the above description.

Supplementary Note 1

There is provided a radiography system including: an electronic cassette that detects a radiographic image based on radiation which has been emitted from a radiation generation apparatus and transmitted through a subject; a console that communicates with a use cassette that is selected from registered cassettes, which are the electronic cassettes registered in advance, and is set as the electronic cassette used for radiography to acquire the radiographic image from the use cassette; a camera image acquisition processor that acquires a camera image, which is obtained by capturing a usage environment including a place in which the electronic cassette is used and a periphery of the place, from an optical camera that captures the usage environment; an in-image cassette detection processor that detects the electronic cassette included in the camera image on the basis of the camera image; an identification information acquisition processor that acquires identification information of the electronic cassette detected from the camera image; a collation processor that collates the identification information with registration information of the registered cassettes registered in the console; and a use cassette setting processor that determines whether the electronic cassette included in the camera image is the registered cassette on the basis of a collation result of the collation processor and sets the electronic cassette determined to be the registered cassette as the use cassette.

Inventions described in the following Supplementary Notes 2 and 3 can be understood from the above description.

Supplementary Note 2

There is provided an operation program that causes a computer to execute a process performed by a radiography system including an electronic cassette that detects a radiographic image based on radiation which has been emitted from a radiation generation apparatus and transmitted through a subject and a console that communicates with a use cassette that is selected from registered cassettes, which are the electronic cassettes registered in advance, and is set as the electronic cassette used for radiography to acquire the radiographic image from the use cassette. The process includes: a camera image acquisition step of acquiring a camera image, which is obtained by capturing a usage environment including a place in which the electronic cassette is used and a periphery of the place, from an optical camera that captures the usage environment; an in-image cassette detection step of detecting the electronic cassette included in the camera image on the basis of the camera image; an identification information acquisition step of acquiring identification information of the electronic cassette detected from the camera image; a collation step of collating the identification information with registration information of the registered cassettes registered in the console; and a use cassette setting step of determining whether the electronic cassette included in the camera image is the registered cassette on the basis of a collation result in the collation step and setting the electronic cassette determined to be the registered cassette as the use cassette.

Supplementary Note 3

There is provided an electronic cassette selection operation receiving device which is used in a radiography system including an electronic cassette that detects a radiographic image based on radiation which has been emitted from a radiation generation apparatus and transmitted through a subject and a console that communicates with a use cassette that is selected from registered cassettes, which are the electronic cassettes registered in advance, and is set as the electronic cassette used for radiography to acquire the radiographic image from the use cassette and receives an operation of selecting the electronic cassette. The electronic cassette selection operation receiving device includes: a camera image acquisition unit that acquires a camera image, which is obtained by capturing a usage environment including a place in which the electronic cassette is used and a periphery of the place, from an optical camera that captures the usage environment; an in-image cassette detection unit that detects the electronic cassette included in the camera image on the basis of the camera image; an identification information acquisition unit that acquires identification information of the electronic cassette detected from the camera image; a collation unit that collates the identification information with registration information of the registered cassettes registered in the console; and a use cassette setting unit that determines whether the electronic cassette included in the camera image is the registered cassette on the basis of a collation result of the collation unit and sets the electronic cassette determined to be the registered cassette as the use cassette.

Supplementary Note 4

There is provided a radiography system including: an electronic cassette that detects a radiographic image based on radiation which has been emitted from a radiation generation apparatus and transmitted through a subject; a console that communicates with a use cassette that is selected from registered cassettes, which are the electronic cassettes registered in advance, and is set as the electronic cassette used for radiography to acquire the radiographic image from the use cassette; a camera image acquisition unit that acquires a camera image, which is obtained by capturing a usage environment including a place in which the electronic cassette is used and a periphery of the place, from an optical camera that captures the usage environment; an in-image cassette detection unit that detects the electronic cassette included in the camera image on the basis of the camera image; an identification information acquisition unit that acquires identification information of the electronic cassette detected from the camera image; a collation unit that collates the identification information with registration information of the registered cassettes registered in the console; a use cassette setting unit that determines whether the electronic cassette included in the camera image is the registered cassette on the basis of a collation result of the collation unit and sets the electronic cassette determined to be the registered cassette as the use cassette; and an imaging order acquisition unit that acquires, from the console, an imaging order to perform radiography which includes suitability information for determining whether the electronic cassette used for the radiography is suitable. In a case in which the imaging order is an order to perform long-length imaging in which two or more electronic cassettes are arranged in a line, radiography is performed, a plurality of radiographic images detected by each electronic cassette are combined to generate one radiographic image indicating a long imaging range, the use cassette setting unit sets a plurality of the registered cassettes included in the camera image as the use cassettes.

Supplementary Note 5

In the radiography system according to Supplementary Note 4, the use cassette setting unit outputs a warning in a case in which the plurality of registered cassettes designated by the imaging order are not included in the camera image.

Supplementary Note 6

In the radiography system according to Supplementary Note 4 or 5, the use cassette setting unit outputs a warning in a case in which the registered cassette suitable for the imaging order is not included in the camera image.

The invention is not limited to the X-rays and can also be applied to a case in which other types of radiation including γ-rays are used.

The invention is not limited to each of the above-described embodiments and can adopt various configurations without departing from the scope and spirit of the invention. In addition, the invention can be applied to a program and a storage medium storing the program.

EXPLANATION OF REFERENCES 10, 100: X-ray imaging system
11: X-ray generation apparatus
12: X-ray imaging apparatus
13, 94: X-ray source
13a: X-ray tube
13b: irradiation field limiter
13c: support
14: radiation source control device
16, 16A, 16B, 16C, 16D, 16E: electronic cassette
17: console
21: bed
22: cradle
23: irradiation switch
26, 92: camera
28: housing
29: communication unit
31: battery
32: marker
33, 96: touch panel
34: input device
35: storage device
36: memory
38: data bus
39: speaker
41: CPU
43: network
44: server
50: operation program
51: GUI controller
52: cassette controller
53: X-ray image processing unit
54: network communication unit
55: search processing unit
57: registered cassette information
58: use cassette setting information
59: imaging order information
61: imaging order display screen
62: patient information display region
63: imaging order display region
63a: display field
64: image display region
66: cassette selection button
67: camera operation button
68: setting button
69: use cassette selection screen
72: in-image cassette detection unit
73: identification information acquisition unit
74: use cassette setting unit
76: camera image
77: in-image cassette region
84: indicator
86: request signal transmission unit
93: treatment cart
H: subject
OP: operator

What is claimed is:

1. A radiography system comprising:
an electronic cassette that detects a radiographic image based on radiation which has been emitted from a radiation generation apparatus and transmitted through a subject;
a console that communicates with a use cassette that is selected from registered cassettes, which are the electronic cassettes registered in advance, and is set as the electronic cassette used for radiography to acquire the radiographic image from the use cassette;
a camera image acquisition unit that acquires a camera image, which is obtained by capturing a usage environment including a place in which the electronic cassette is used and a periphery of the place, from an optical camera that captures the usage environment;
an in-image cassette detection unit that detects the electronic cassette included in the camera image on the basis of the camera image;
an identification information acquisition unit that acquires identification information of the electronic cassette detected from the camera image;
a collation unit that collates the identification information with registration information of the registered cassettes registered in the console;
a use cassette setting unit that determines whether the electronic cassette included in the camera image is the registered cassette on the basis of a collation result of the collation unit and sets the electronic cassette determined to be the registered cassette as the use cassette,
a direction detection unit that detects a direction in which the electronic cassette is present in the usage environment on the basis of the camera image; and
a request signal transmission unit that transmits an identification information request signal for requesting the identification information to the electronic cassette,
wherein, in a case in which the electronic cassette is included in the camera image, the request signal transmission unit transmits the identification information request signal in the direction detected by the direction detection unit and receives the identification information as a response from the electronic cassette, and
the identification information acquisition unit acquires the identification information received by the request signal transmission unit.

2. The radiography system according to claim 1, wherein the camera image is a motion picture or a still image.

3. The radiography system according to claim 1, wherein the camera is provided in the radiation generation apparatus or is provided in a room in a case in which the usage environment is an indoor environment.

4. The radiography system according to claim 1,
wherein the identification information includes a cassette ID which includes a character string uniquely given to each electronic cassette.

5. The radiography system according to claim 4,
wherein, in a case in which an ID marker indicating the cassette ID is attached to an outer surface of the electronic cassette, the identification information acquisition unit detects the ID marker from the camera image and acquires the cassette ID, and
the collation unit collates the cassette ID with the registration information.

6. The radiography system according to claim 1,
wherein, in a case in which a light source that emits identification light which is light indicating the identification information is provided in the electronic cassette, the identification information acquisition unit detects the identification light from the camera image and acquires the identification information.

7. The radiography system according to claim 6,
wherein the identification light is identified on the basis of at least one of a color, a lighting pattern, or a lighting time.

8. The radiography system according to claim 1,
wherein, in a case in which the response is not received, the identification information acquisition unit transmits, to the electronic cassette, a status change command to change a status of the electronic cassette to a status in which the electronic cassette is capable of responding to the identification information request signal.

9. The radiography system according to claim 1,
wherein the identification information acquisition unit outputs a warning in a case in which the electronic cassette is included in the camera image, but the identification information is not capable of being acquired from the electronic cassette.

10. The radiography system according to claim 1,
wherein, in a case in which the electronic cassette detected in the camera image has been set as the use cassette, the use cassette setting unit notifies that the electronic cassette detected in the camera image has been set as the use cassette through a notification unit.

11. The radiography system according to claim 10,
wherein the notification unit is provided in the radiation generation apparatus.

12. The radiography system according to claim 1,
wherein, in a case in which the electronic cassette is included in the camera image, but is not the registered cassette, the use cassette setting unit outputs a warning indicating that the electronic cassette is not the registered cassette.

13. The radiography system according to claim 12,
wherein, in a case in which the electronic cassette is included in the camera image, but is not the registered cassette, the use cassette setting unit performs a process of inquiring whether to register the electronic cassette as the registered cassette in the console.

14. The radiography system according to claim 1,
wherein, in a case in which the use cassette has been set in the console and the registered cassette different from the set use cassette is newly detected from the camera image, the use cassette setting unit changes the newly detected registered cassette to the use cassette.

15. The radiography system according to claim 14,
wherein, in a case in which the use cassette has been set in the console and the registered cassette different from the use cassette is newly detected from the camera image, the use cassette setting unit performs a process of inquiring whether to change the newly detected registered cassette to the use cassette.

16. The radiography system according to claim 1, further comprising:
an imaging order acquisition unit that acquires an imaging order to perform radiography,
wherein, in a case in which the electronic cassette detected in the camera image is determined to be the registered cassette, the use cassette setting unit collates the content of the imaging order with specification information of the registered cassettes registered in advance, determines suitability of the registered cassettes for the imaging order, and sets the registered cassette that is suitable for the imaging order as the use cassette.

17. The radiography system according to claim 1,
wherein, during the setting of the electronic cassette detected in the camera image as the use cassette, in a case in which the detected electronic cassette is set as the use cassette and a status of the set use cassette is in a power saving mode, the use cassette setting unit changes the status to a ready status in which radiography is capable of being performed.

18. A method for operating a radiography system comprising an electronic cassette that detects a radiographic image based on radiation which has been emitted from a radiation generation apparatus and transmitted through a subject and a console that communicates with a use cassette that is selected from registered cassettes, which are the electronic cassettes registered in advance, and is set as the electronic cassette used for radiography to acquire the radiographic image from the use cassette, the method comprising:
a camera image acquisition step of acquiring a camera image, which is obtained by capturing a usage environment including a place in which the electronic cassette is used and a periphery of the place, from an optical camera that captures the usage environment;
an in-image cassette detection step of detecting the electronic cassette included in the camera image on the basis of the camera image;
an identification information acquisition step of acquiring identification information of the electronic cassette detected from the camera image;
a collation step of collating the identification information with registration information of the registered cassettes registered in the console;
a use cassette setting step of determining whether the electronic cassette included in the camera image is the registered cassette on the basis of a collation result in the collation step and setting the electronic cassette determined to be the registered cassette as the use cassette,
a direction detection step of detecting a direction in which the electronic cassette is present in the usage environment on the basis of the camera image; and
a request signal transmission step of transmitting an identification information request signal for requesting the identification information to the electronic cassette,
wherein, in a case in which the electronic cassette is included in the camera image, the identification information request signal is transmitted in the direction detected in the direction detection step and the identification information is received as a response from the electronic cassette.

\* \* \* \* \*